United States Patent [19]
Mitchell et al.

[11] Patent Number: 6,069,277
[45] Date of Patent: *May 30, 2000

[54] AMINATION OF ELECTROPHILIC AROMATIC COMPOUNDS BY VICARIOUS NUCLEOPHILIC SUBSTITUTION

[75] Inventors: Alexander R. Mitchell; Philip F. Pagoria; Robert D. Schmidt, all of Livermore, Calif.

[73] Assignee: The Regents of the University of California, Oakland, Calif.

[*] Notice: This patent is subject to a terminal disclaimer.

[21] Appl. No.: 08/967,914

[22] Filed: Nov. 12, 1997

Related U.S. Application Data

[63] Continuation-in-part of application No. PCT/US96/06663, May 10, 1996, which is a continuation-in-part of application No. 08/440,017, May 12, 1995, Pat. No. 5,569,783, and a continuation-in-part of application No. 08/440,024, May 12, 1995, Pat. No. 5,633,406.

[51] Int. Cl.$^7$ .................................................. C07C 209/02
[52] U.S. Cl. ........................... 564/395; 564/408; 564/441; 568/932; 568/934
[58] Field of Search ...................... 564/395, 408, 564/441; 568/932, 934

[56] References Cited

U.S. PATENT DOCUMENTS 4,032,377  6/1977  Benziger et al. ....................... 149/105

*Primary Examiner*—Brian M. Burn
*Attorney, Agent, or Firm*—Peters, Verny, Jones & Biksa, LLP

[57] ABSTRACT

The present invention relates to a process to aminate electrophilic aromatic compounds by vicarious nucleophilic substitution of hydrogen using quaternary hydrazinium salts. The use of trialkylhydrazinium halide, e.g., trimethylhydrazinium iodide, as well as hydroxylamine, alkoxylamines, and 4-amino-1,2,4-triazole to produce aminated aromatic structures, such as 1,3-diamino-2,4,6-trinitrobenzene (DATB), 1,3,5-triamino-2,4,6-trinitrobenzene (TATB) and 3,5-diamino-2,4,6-trinitrotoluene (DATNT), is described. DATB and TATB are useful insensitive high explosives. TATB is also used for the preparation of benzenehexamine, a starting material for the synthesis of novel materials (optical imaging devices, liquid crystals, ferromagnetic compounds).

20 Claims, No Drawings

_6,069,277_

AMINATION OF ELECTROPHILIC AROMATIC COMPOUNDS BY VICARIOUS NUCLEOPHILIC SUBSTITUTION

RELATED APPLICATIONS

This application is a continuation-in-part and claims priority on International Application PCT/US96/06663, filed May 10, 1996, which is a continuation-in-part of U.S. Ser. No. 08/440,017, filed May 12, 1995, now U.S. Pat. No. 5,569,783, and a continuation-in-part of U.S. Ser. No. 08/440,024, filed May 12, 1995, now U.S. Pat. No. 5,633,406, all of which are incorporated herein by reference in their entirety.

ORIGIN OF THE INVENTION

The United States Government has rights in this invention pursuant to Contract No. W-7405-ENG-48 between the U.S. Department of Energy and the University of California, for the operation of Lawrence Livermore National Laboratory, Livermore, Calif.

BACKGROUND OF THE INVENTION

1. Field of the Invention for Amination

The present invention concerns the mono- and/or polyamination of electrophilic aromatic compounds. In particular, the present invention concerns the discovery and use of quaternary hydrazinium salts, e.g., 1,1,1-trisubstituted hydrazinium salts, for vicarious nucleophilic substitution (VNS) of hydrogen, which provide new and improved syntheses of mono and/or poly amino-aromatic compounds, such as 1,3-diamino-2,4,6-trinitrobenzene (DATB) and 1,3,5-triamino-2,4,6-trinitrobenzene (TATB). The present invention also concerns the use of 4-amino-1,2,4-triazole, as well as hydroxylamnine and its O-alkyl derivatives, to provide new and improved syntheses of aromatic amine compounds, such as DATB and TATB, by VNS reactions.

2. Description of the Problem and Related Art

The amination of organic aromatic compounds (both carbocyclic and heterocyclic) occurs according to a number of reactions known in the art. However, the methods of the art often are dangerous, require special equipment, have problematic side reactions, separation problems, hazardous reagents, environmental problems and the like.

Some explosives are more sensitive to shock and heat than others having a similar structure. Studies of explosives based on the benzene ring include, for example, 1,3,5-trinitrobenzene (TNB), 2,4,6-trinitrotoluene (TNT), 1-amino-2,4,6-trinitrobenzene (TNA) (aka picramide), 1,3-diamino-2,4,6-trinitrobenzene (DATB) and 1,3,5-triamino-2,4,6-trinitrobenzene (TATB). Although these compounds have much in common, the shock initiation thresholds, that is, the shock pressure required to cause detonation in 50% of the tests, vary widely. Table 1 shows the pattern.

TABLE 1

SHOCK INITIATION THRESHOLD OF EXPLOSIVES

| Compound | Pressure (kilobars) |
|---|---|
| TNB | 17 |
| TNT | 21 |
| TNA | 30 |
| DATB | 46 |
| TATB | 75 |

While not wanting to be bound by theory, it appears that adding amino groups to a nitro-substituted benzene ring raises the shock initiation threshold. This pattern occurs, because as the networks of hydrogen bonds increase, the networks absorb energy from a shock front and reduce the amount of shock that goes to the ring itself. See W. Worthy in "Shock Sensitivity of Explosives Clarified", _Chemical and Engineering News_, p. 25, (Aug. 10, 1987) for further discussion.

It follows that DATB and TATB are highly desirable, insensitive explosives that are used primarily in specialty applications. Part of the reason that they are used in special as opposed to general explosive applications is high cost. They are too expensive to use in ordinary applications when other less expensive explosives can be used. One reason that TATB is expensive is that it is usually prepared from 1,3,5-trichlorobenzene which is expensive and is not generally available from domestic suppliers. The ammonium chloride byproduct ($NH_4Cl$) is difficult to remove completely and may cause compatibility problems in certain types of ordnance (e.g., U.S. Pat No. 4,032,377).

Alternative preparations of aminoaromatic compounds were sought, and include:

T. M. Benziger, U.S. Pat No. 4,032,377 discloses a preparation of TATB by nitration of 1,3,5-trichlorobenzene to 1,3,5-trichloro-2,4,6-trinitrobenzene followed by treatment with ammonia to produce TATB. This patent also discloses the use of water to separate the byproduct ammonium chloride.

D. G. Ott and T. M. Benziger, U.S. Pat No. 4,952,733 and _Journal of Energetic Materials_, vol. 5, pp. 343–354 (1987) disclose a preparation of TATB by nitration of 3,5-dichloroanisole to produce 3,5-dichloro-2,4,6-trinitroanisole which is chlorinated to give 1,3,5-trichloro-2,4,6-trinitrobenzene which is ammonolyzed to give TATB.

Additional art of interest includes, for example:

R. L. Atkins et al., in U.S. Pat No. 4,248,798 disclose a new method for preparing pentanitroaniline (PNA) and triaminotrinitrobenzene (TATB) from TNT. TNT is first reduced using $H_2S$ to 4-amino-2,6-dinitrotoluene then nitrated using nitric acid/sulfuric acid to pentanitroaniline followed by reaction with ammonia to produce the TATB.

M. Makosza et al., review and discuss "Vicarious Nucleophilic Substitution of Hydrogen", in _Accounts of Chemical Research_, vol. 20, pp. 282–9 (1987), and teach the substitution of polynitrobenzene structures with a number of non-nitrogen containing vicarious nucleophilic substitution reagents. No nitrogen-containing reagents are disclosed or suggested.

A. R. Katritzky and K. S. Laurenzo, _Journal of Organic Chemistry_, vol. 51, pp. 5039–5040 (1986) disclose monoamination of nitrobenzene and some substituted nitrobenzenes to give 4-nitroanilines by VNS reactions. The same authors, in the _Journal of Organic Chemistry_, vol. 53, pp. 3978–3982 (1988) disclose the use of a series of 4-(alkylamino)-1,2,4-triazoles to transfer the alkylamino group to the 4-position of nitrobenzene and 3-substituted nitrobenzenes by VNS. Only monoamination is taught or suggested.

T. Urbanski et al., _Journal of Scientific and Industrial Research_ (India), vol. 37, p. 250–5 (1978), disclose the standard preparation and properties of several heat resistant explosives including DATB and TATB.

J. R. Holden et al., U.S. Naval Ordnance Laboratory, White Oak, Md., NAVORD Report 6299 (March 1959), disclose the properties of DATB.

S. K. Yasuda et al., in _Journal of Chromatography_, vol. 71, p. 484–86 (1972) discuss the separation and identification of 12 impurities of TATB by two dimensional thin-layer chromatography.

M. Makosza et al., *Journal of Organic Chemistry*, vol. 57, p. 4784–5 (1992), disclose the mono-amination of nitrobenzenes with sulfenamides via vicarious nucleophilic substitution of hydrogen. See also U.S. Pat. No. 5,262,539.

W. P. Norris et al., "CL-14, A New Dense, Insensitive, High Explosive", Naval Weapons Center, China Lake, Calif., Report No. TP 6597 (Unclassified), May 1985, disclose the use of hydroxylamine to di-aminate 4,6-dinitrobenzofuroxan (DNBF) thereby producing 5,7-diamino-4,6-dinitrobenzofuroxan (CL-14).

R. L. Atkins et al., in the *Journal of Organic Chemistry*, vol. 51, pp. 3261–3266 (1986), disclose the synthesis of a number of polynitro compounds, including TATB. Pentanitroaniline is reacted with ammonia to produce TATB.

T. R. Gibbs et al., *LASL Explosives Properties Data* (*University of California Press*, Berkeley, Calif., 1980.

B. M. Dobratz, *LLNL Explosives Handbook: Properties of Chemical Explosives and Explosive Simulants*, Lawrence Livermore National Laboratory, Livermore, Calif., UCRL-52997 (Mar. 16, 1981).

German patent, Ger. Offen DE 3,612,238) teaches the use of TATB to prepare components of lyotropic liquid-crystal phases for use in display devices.

TATB is also valuable in non-explosive applications. K. Praefake and B. Kohne, Ger. Offen. DE 3,612,238 disclose the use of TATB to prepare hexaaminobenzene derivatives which are used as components of lyotropic liquid-crystal phases, which can be used in display devices.

Additional art of interest includes, for example:

J. Meisenheimer et al., in *Chemische Berichte*, vol. 39, pp. 2533–2542 (1906) describe the di-amination of 1,3-dinitrobenzene with hydroxylamine under basic conditions to yield 2,4-dinitro-1,3-phenylenediamine. S. Seko in U.S. Pat. No. 5,466,871 extends the work of Meisenheimer by employing O-alkylhydroxylamines to monoaminate substituted nitrobenzene derivatives thereby providing various nitroanilines.

J. A. Hoffman and C. F. McDonough, U.S. Pat. No. 3,278,604 and J. C. Dacons et al., in U.S. Pat. No. 3,394,183 both disclose the preparation of DATB via sulfonation and nitration (2 steps) of 1,3-dimethoxy-2,4,6-trinitrobenzene (DMTNB) which is then aminated to give DATB.

J. G. Kaey and E. F. V. Scriven in Chemical Specialties USA 91 Symposium disclose the regiospecific synthesis of 1-substituted-1,2,4-triazoles using 4-amino-1,2,4-triazole.

None of these references individually or collectively teach or suggest the present invention.

All patents, applications, articles, standards, references, etc., cited in this application and incorporated herein by reference.

There is a need for new processes which are milder and more environmentally benign to convert aromatic compounds to mono- and/or polyamino aromatic compounds, such as DATB, TATB or mixtures thereof. The present invention provides such useful processes which avoid strong acids ($H_2SO_4$, $HNO_3$), avoid elevated temperatures (100–150° C.), and avoid the need for noxious materials such as ammonia, thionyl chloride or hydrogen sulfide. The present invention provides useful processes which are also environmentally benign.

SUMMARY OF THE INVENTION

The present invention concerns the monoamination or polyamination of electrophilic aromatic compounds. In particular, the reagents used are 1,1,1-trialkylhydrazinium salts (e.g., halides) or 4-amino-1,2,4-triazole, hydroxylamine or O-alkylhydroxylamine, wherein alkyl is selected from groups having 1 to 10 carbon atoms.

The present invention relates to a process to produce one or more monoamino, diamino or polyamino aromatic compounds, which process comprises:

(a) reacting at ambient pressure and a temperature of between about 0 and 50° C. for between about 0.1 and 24 hr, a trinitroaromatic starting material compound V:

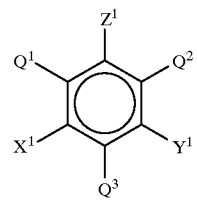

wherein $Q^1$, $Q^2$, $Q^3$, $X^1$, $Y^1$, and $Z^1$ are each independently selected from the group consisting of —H, —$NO_2$, —$CH_3$, —COOH, —$OCH_3$, and —$NH_2$, with the proviso that at least 1 of $Q^1$, $Q^2$, $Q^3$, $X^1$, $Y^1$, and $Z^1$ is hydrogen, with (i) an effective amount of quaternary hydrazinium salts, such as 1,1,1,-trialkylhydrazinium salt wherein alkyl is selected from methyl, ethyl, propyl, butyl or benzyl and the anion is selected from chloride, bromide, iodide, fluoride, sulfate, hydroxide, mesylate, triflate, or tetrafluoroborate, or (ii) 4-amino-1,2,4-triazole, hydroxylamine or O-alkylhydroxylamine wherein alkyl has 1–10 carbon atoms;

in the presence of a strong base selected from sodium butoxide, potassium butoxide, potassium propoxide, sodium propoxide, sodium ethoxide, potassium ethoxide, sodium methoxide, potassium methoxide, and combinations thereof;

in a solvent selected from the group consisting of methanol, ethanol, propanol, butanol, dimethylsulphoxide, N-methylpyrrolidone, hexamethylphosphorarnide, dimethylformamide, dimethylacetamide and mixtures thereof, provided that when alcohols are present primarily DATB and picramide are formed; and (b) isolating the monoamino, diamino or polyamino aromatic compound produced.

In a preferred embodiment, 4-amino-1,2,4-triazo is used with the proviso that only diamino or polyamino aromatic compounds are produced.

In another preferred embodiment the hydroxylamine and O-alkylhydroxylamine are used with the proviso that only diamino- or polyamino- aromatic compounds are produced.

The present invention also relates to a process to produce 1,3-diamino- 2,4,6-trinitrobenzene (DATB), 1,3,5-triamino-2,4,6-trinitrobenzene (TATB) or 3,5-diamino-2,4,6-trinitrotoluene (DATNT) by:

(a) reacting at ambient pressure and a temperature of between about 0 and 50° C. for between about 0.1 and 24 hr, a trinitroaromatic starting material compound:

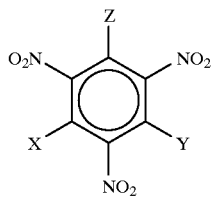

(V)

wherein X, Y, and Z are each independently selected from the group consisting of —H, —CH₃, and —NH₂, with the proviso that at least 1 of X, Y, and Z are hydrogen;

with an amount effective to produce DATB, TATB, or DATNT of 1,1,1-trialkyl hydrazinium salt wherein alkyl is selected from methyl, ethyl, propyl, butyl, or benzyl, and the anion of the salt is selected from chloride, bromide, iodide, fluoride, sulfate, hydroxide, mesylate, triflate, tetrafluoroborate and the like;

in the presence of a strong base selected from sodium butoxide, potassium butoxide, potassium propoxide, sodium propoxide, sodium ethoxide, potassium ethoxide, sodium methoxide, potassium methoxide, and combinations thereof;

in a solvent selected from the group consisting of methanol, ethanol, propanol, butanol, dimethylsulphoxide, N-methylpyrrolidone, hexamethylphosphoramide, dimethylformamide, dimethylacetamide and mixtures thereof, provided that when alcohols are present primarily DATB and picramide are formed; and (b) isolating the DATB, TATB or DATNT produced.

Preferably, X, Y and Z are each independently selected from —H, —CH₃, or NH₂.

In another aspect, the present invention concerns a process to produce 1,3-diamino-2,4,6-trinitrobenzene (DATB) or 1,3,5-triamino-2,4,6-trinitrobenzene (TATB):

(a) by obtaining an aromatic compound of the structure:

(III)

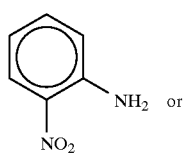

(IV)

mixtures thereof from commercial sources or by:
(i) reacting

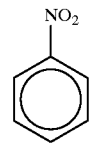

at a temperature of between about 0 and 50° C. for between about 0.1 and 24 hr with an effective amount of 1,1,1-trialkylhydrazinium salt wherein alkyl is selected from methyl, ethyl, propyl, butyl, or benzyl and the anion of the salt is selected from chloride, bromide, iodide, fluoride, sulfate, hydroxide, mesylate, triflate, tetrafluoroboratesand the like to produce compound III or compound IV;

in the presence of a strong base selected from sodium butoxide, potassium butoxide, potassium propoxide, sodium propoxide, sodium ethoxide, potassium ethoxide, sodium methoxide, potassium methoxide, or combinations thereof;

in a solvent selected from the group consisting of methanol, ethanol, propanol, butanol, dimethylsulfoxide, N-methylpyrrolidone, hexamethylphosphoramide, dimethylformamide, dimethylacetamide, or mixtures thereof, and isolating the product which is compound III and/or IV;

(ii) or nitrating aniline using a mixture of nitric acid and sulfuric acid to produce compounds III and IV; or (iii) nitrating acetanilide using a mixture of nitric acid and sulfuric acid to produce 4-nitroacetanilide and nitrating further using a mixture of nitric acid and sulfuric acid to produce compound VI;

(b) reacting 2-nitroaniline, 4-nitroaniline or combinations thereof with a nitric acid, and sulfuric acid mixture under conditions to produce 2,4,6-trinitroaniline (VI);

(c) reacting at ambient pressure and a temperature of between about 0 and 50° C. for between about 0.1 and 24 hr a trinitroaromatic compound:

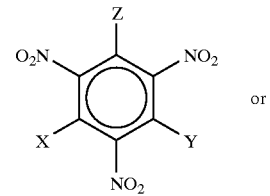

(V)

or

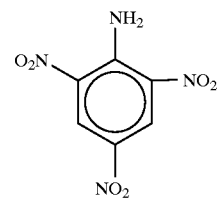

(VI)

wherein X, Y, and Z are each independently selected from the group consisting of —H, and —NH₂, with the proviso that at least 1 of X, Y, and Z is hydrogen;

with an effective amount of 1,1,1-trialkylhydrazinium salt wherein alkyl is selected from methyl, ethyl, propyl, butyl, or benzyl, and the anion of the salt is selected from chloride, bromide, iodide, fluoride, sulfate, hydroxide, mesylate, triflate, tetrafluoroborate and the like.

in the presence of a base selected from the group consisting of sodium butoxide, potassium butoxide, potassium propoxide, sodium propoxide, sodium ethoxide, potassium ethoxide, sodium methoxide, potassium methoxide, and mixtures thereof;

in a solvent selected from the group consisting of methanol, ethanol, propanol, butanol, dimethylsulphoxide, N-methylpyrrolidone, hexamethylphosphoramide, dimethylformamide, dimethylacetamide, and mixtures thereof; and (d) isolating the DATB or TATB produced.

Preferably, DATB is produced when the 1,1,1-trialkylhydrazinium salt is present in between about 1.9 and 2.3 molar equivalents per mole of compound V.

Preferably, starting material is selected from 1,3,5-trinitrobenzene, 2,4,6-trinitroaniline, or 1,3-diamino-2,4,6-trinitrobenzene.

Preferably, the 1,1,1-trialkylhydrazinium salt is 1,1,1-trimethylhydrazinium iodide.

Preferably, the strong base is selected from sodium methoxide or potassium tert-butoxide.

Preferably, the solvents are selected from the group consisting of methanol, ethanol, propanol, butanol, dimethylsulphoxide, N-methylpyrrolidone, hexamethylphosphoramide, dimethylformamide, dimethylacetamide and mixtures thereof, provided that when alcohols are present primarily DATB and picramide are formed.

Preferably, TATB is produced when the 1,1,1-trialkylhydrazinium salt is present in between about 3.9 and 5.5 molar equivalents per mole of compound V.

In another embodiment, the present process includes reacting:

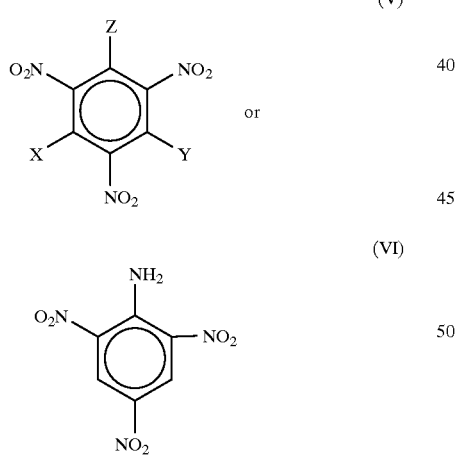

wherein X, Y, and Z are each independently selected from the group consisting of —H, —CH₃, and —NH₂, with the proviso that at least 1 of X, Y, and Z is hydrogen, with an effective amount of 1,1,1-trialkylhydrazinium salt wherein alkyl is selected from methyl, ethyl, propyl or butyl and anion is selected from chloride, bromide, iodide, fluoride, sulfate, hydroxide, mesylate, triflate, tetrafluoroborate, and the like.

in the presence of a base selected from the group consisting of sodium butoxide, potassium butoxide, potassium propoxide, sodium propoxide, sodium ethoxide, potassium ethoxide, sodium methoxide, potassium methoxide, and mixtures thereof;

in a solvent selected from the group consisting of methanol, ethanol, propanol, butanol, dimethylsulphoxide, N-methylpyrrolidone, hexamethylphosphoramide, dimethylformamide, dimethylacetamide, and mixtures thereof; and (B) isolating the DATB or TATB produced.

In another embodiment of the process, the reaction temperature is between about 10 and 30° C.

In another aspect, the present invention concerns a process to produce aminated aromatic compounds, which process comprises:

(A) obtaining an electrophilic aromatic compound which is selected from benzene, naphthalene, quinoline, quinoxaline, pyridine, pyrazine, pyrimidine, pyrazole, imidazole, and the like. The electrophilic aromatic compound may be substituted with one or more electron withdrawing groups, such as —SO₃H, —NO₂, —CN, —CF₃, —COOR, —COR, Cl, Br, —NO₂ and the like which enhance the amination.

Examples from the nitrobenzenes include:

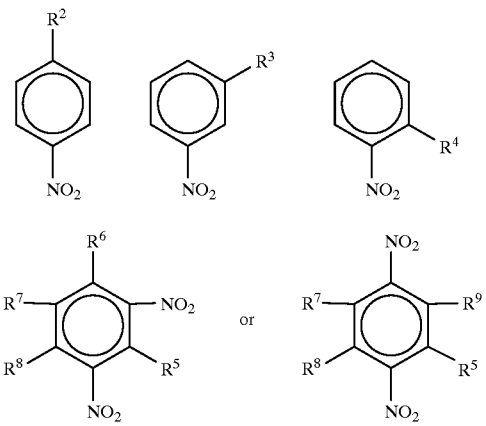

wherein R², R³, and R⁴ are each independently selected from —H, —CH₃, —F, —Cl, —Br, —I, —CN, —COOH, —COOR¹¹ where R¹¹ is C1 to C10 alkyl, or —OCH₃, and R⁵–R⁹ are each independently selected from —H, —CH₃, —F, —Cl, —Br, —I, —CN, —COOH, or —OCH₃ or mixtures thereof;

(B) reacting a nitro aromatic compound at ambient pressure and a temperature of between about 0 and 50° C. for between about 0.1 and 24 hr; with an effective amount of 1,1-dialkyl-1,2-di-R-(where R=hydrogen, alkyl or aryl) hydrazinium salt wherein dialkyl is selected from methyl, ethyl, propyl, butyl, hexyl, cyclohexyl, (—CH₂ (CH₂)ₙ CH₂—) —(CH₂CH₂)O (CH₂CH₂)—, hexyl, dodecyl, or pyridyl, and n is 1 to 10. R is selected from H, C1–C20 alkyl, or aryl, and anion is selected from chloride, bromide, iodide, fluoride, sulfate, hydroxide, mesylate, triflate, tetrafluoroborate, and the like.

in the presence of a base selected from the group consisting of sodium butoxide, potassium butoxide, potassium propoxide, sodium propoxide, sodium ethoxide, potassium ethoxide, sodium methoxide, potassium methoxide, and mixtures thereof;

in a solvent selected from the group consisting of methanol, ethanol, propanol, butanol, dimethylsulphoxide, N-methylpyrrolidone, hexamethylphosphoramide, dimethylformamide, dimethylacetamide, and mixtures thereof; and (c) isolating the monoamino, diamino or triaminosubstituted nitroaromatic compound produced.

In another aspect, the present invention concerns a process to produce 1,3-diamino-2,4,6-trinitrobenzene (DATB) or 1,3,5-triamino-2,4,6,-trinitrobenzene (TATB) by:

(a) reacting at ambient pressure and a temperature of between about 0 and 50° C. for between about 0.1 and 24 hr, a trinitroaromatic compound of structure V:

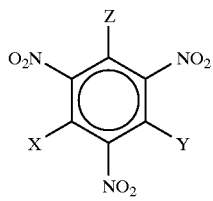

(V)

wherein X, Y, and Z are each independently selected from the group consisting of —H and —NH$_2$, with the proviso that at least 1 of X, Y, and Z is hydrogen, with an effective amount of 4-amino-1,2,4-triazole (ATA) to produce DATB or TATB or hydroxylamine or O-alkylhydroxylamine, wherein alkyl has 1 to 10 carbon atoms, to primarily produce DATB;

in the presence of a strong base selected from sodium butoxide, potassium butoxide, potassium propoxide, sodium propoxide, sodium ethoxide, potassium ethoxide, sodium methoxide, potassium methoxide, and combinations thereof;

in a solvent selected from the group consisting of methanol, ethanol, propanol, butanol, dimethylsulphoxide, N-methylpyrrolidone, hexamethylphosphoramide, dimethylformamide, dimethylacetamide and mixtures thereof, provided that when alcohols are present or hydroxylamine or its O-alkyl derivatives replace ATA primarily DATB is formed; and (b) isolating the DATB or TATB produced.

In another aspect, the present invention concerns a process to produce 1,3-diamino-2,4,6-trinitrobenzene (DATB) or 1,3,5-triamino-2,4,6,-trinitrobenzene (TATB):

(a) by obtaining an aromatic compound of the structure:

(III)

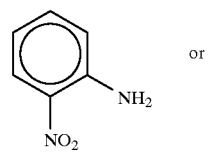

(IV)

mixtures thereof from commercial sources or by:
(i) reacting

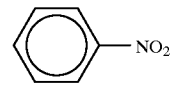

at a temperature of between about 0 and 50° C. for between about 0.1 and 24 hr with an effective amount of ATA, hydroxylamine or O-alkylhydroxylamine to produce mono or diamination, in the presence of a strong base selected from sodium butoxide, potassium butoxide, potassium propoxide, sodium propoxide, sodium ethoxide, potassium ethoxide, sodium methoxide, potassium methoxide, and combinations thereof;

in a solvent selected from the group consisting of dimethylsulphoxide, N-methylpyrrolidone, hexamethylphosphoramide, dimethylformamide, dimethylacetamide, or mixtures thereof, and isolating the product which is compound III;

(ii) or nitrating aniline using a mixture of nitric acid and sulfuric acid to produce compounds III and IV; or (iii) nitrating acetanilide using a mixture of nitric acid and sulfuric acid to produce 4-nitroacetanilide and nitrating further using a mixture of nitric acid and sulfuric acid to produce VI;

(b) reacting 2-nitroaniline, 4-nitroaniline or combinations thereof with a nitric acid, and sulfuric acid mixture under conditions to produce 2,4,6-trinitroaniline (VI);

(c) reacting at ambient pressure and a temperature of between about 0 and 50° C. for between about 0.1 and 24 hr a trinitroaromatic compound of the structure:

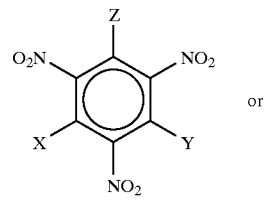

(V)

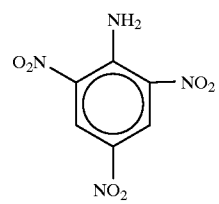

(VI)

wherein X, Y, and Z are each independently selected from the group consisting of —H and —NH$_2$, with the proviso that at least 1 of X, Y, and Z is hydrogen;

with an effective amount of 4-amino-1,2,4-triazole, hydroxylamine or O-alkylhydroxylamine wherein alkyl contains 1 to 10 carbon atoms;

in the presence of a base selected from the group consisting of sodium butoxide, potassium butoxide, potassium propoxide, sodium propoxide, sodium ethoxide, potassium ethoxide, sodium methoxide, potassium methoxide, and mixtures thereof;

in a solvent selected from the group consisting of methanol, ethanol, propanol, butanol, dimethylsulphoxide, N-methylpyrrolidone, hexamethylphosphoramide, dimethylformamide, dimethylacetamide, and mixtures thereof, with the proviso that when alcohol is present or hydroxylamine and its O-alkyl derivatives replace ATA, primarily DATB is produced; and (d) isolating the DATB or TATB produced.

Preferably, DATB is produced when ATA, hydroxyl amine or O-alkylhydroxylamine is present in between about 1.9 and 2.3 molar equivalents per mole of compound V.

Preferably, structure V is selected from 1,3,5-trinitrobenzene, 2,4,6-trinitroaniline, or 1,3-diamino-2,4,6-trinitrobenzene.

Preferably, the strong base is selected from sodium methoxide or potassium tert-butoxide.

Preferably, the solvents are selected from methanol, ethanol, propanol, butanol, dimethylsulphoxide, N-methylpyrrolidone, hexamethylphosphoramide, dimethylformamide, dimethylacetamide and mixtures thereof, provided that when alcohols are present or hydroxylamine and its O-alkyl derivatives replace ATA, primarily DATB and picramide are formed.

Preferably, TATB is produced when ATA is present in between about 3.9 and 5.5 molar equivalents per mole of starting compound V.

Preferably, in all embodiments described herein, 4-amino-1,2,4-triazole, hydroxylamine, or O-alkylhydroxylamine are used with the proviso that diamino or polyamino aromatic compounds are produced.

In another aspect, when the reaction described hereinabove using hydroxyl amine or trialkylhydrazinium iodide (e.g., trimethylhydrazinium iodide) at elevated temperatures between about 70° and 100° C., preferably between about 80 and 100° C., and especially about 90° C., that a good yield of the triamino product, e.g., TATB, is produced.

DETAILED DESCRIPTION OF THE INVENTION AND PREFERRED EMBODIMENTS

Definitions

As used herein for amination of aromatic compounds using the reagents described herein:

"Alkyl" refers to alkyl groups, having 1 to 10 carbon atoms and includes alkylaryl groups such as benzyl or ethylenephenyl (—CH$_2$CH$_2$-phenyl).

"Aromatic compound" refers to any organic compound which has a conjugated ring structure and exhibits aromatic structure properties. It includes carbocyclic structures where only carbon atoms are present having substituents which include any electron withdrawing group recited herein. It includes heterocyclic aromatic compounds as defined herein.

"ATA" refers to 4-amino-1,2,4-triazole.

"DMF" refers to dimethylformamide.

"DMAC" refers to dimethylacetamide.

"DATB" refers to 1,3-diamino-2,4,6-trinitrobenzene.

"DMSO" refers to dimethylsulphoxide.

"Heterocyclic aromatic compound" refers to any organic compound which as a conjugated ring structure, has at least one heteroatom in the ring, e.g., N, O, S, etc. and exhibits aromatic structure properties. Nitrogen containing rings are preferred.

"HMPA" refers to hexamethylphosphoramide.

"NB" refers to nitrobenzene.

"NMP" refers to N-methypyrrolidone.

"NT" refers to nitrotoluene.

"Picramide" or "TNA" refers to 1-amino-2,4,6-trinitrobenzene.

"Salt" refers to the anions described herein. Halide is preferred.

"TATB" refers to 1,3,5-triamino-2,4,6-trinitrobenzene.

"TAHI" refers to trialkylhydrazium iodide.

"TMHI" refers to triamethylhydrazinium iodide.

"TNA" refers to 1-amino-2,4,6-trinitrobenzene.

"TNB" refers to 1,3,5-trinitrobenzene.

"TNT" refers to 2,4,6-trinitrotoluene.

"DATNT" refers to 3,5-diamino-2,4,6-trinitrontoluene.

The present invention includes the preparation of monoamino-, diamino-, or polyamino- aromatic compounds, e.g., DATB, TATB, and DATNT. TATB is also useful in the preparation of liquid crystals.

In the present invention, the starting material, an electrophilic aromatic compound, e.g., a mononitrated, dinitrated or trinitrated aromatic compound or heterocyclic compound, is contacted with strong base in the presence of a solvent at between about 0 and 50° C. and ambient pressure for between about 0.1 and 24 hr, preferably between about 1 and 5 hr. Preferably, the temperature is between about 10 and 30° C., and more preferably about ambient temperature (i.e. 20° C.). The electrophilic aromatic compound is reacted with 1,1,1-trialkylhydrazinium salt to provide amino-substituted aromatic compounds by VNS.

The reaction conditions for the VNS of specific aromatic substrates are described herein below for DATB and/or TATB. Examples include the conversion of 3-substituted nitrobenzenes to the corresponding nitroanilines, and conversion of trinitroarenes to the corresponding polyaminotrinitroarenes.

*Chemical and Engineering News*, May 8, 1995, p. 21 discloses that the Defense Nuclear Agency has given a contract to Thiokol Corp. to dispose of liquid propellant dimethyl hydrazine (fuel from Russian intercontinental ballistic missiles and the starting material for trimethylhydrazinium salts) by converting the fuel into commercial commodity chemicals. Also see H. H. Szmant, *Organic Building Blocks of the Chemical Industry*, John Wiley and Sons, New York, 1989, p. 83.

G. M. Omietanski et al., *Journal of the American Chemical Society*, vol. 78, p. 1211–1213 (1956), disclose the preparation of alkyl and cycloalkyl hydrazinium chlorides. O. Westphal, in *Chem. Ber.*, vol. 74, 759ff (1941), disclose a preparation of quaternized hydrazines.

Quaternary hydrazines are also prepared in situ (via reaction of the appropriate unsymmetrical hydrazine and alkylating reagent) and used directly in a VNS reaction. EXAMPLE 3A (below) describes the reaction of methyl iodide and 1,1-dimethylhydrazine in DMSO to form TMHI which is used without isolation for the conversion of picramide to TATB. Similarly, EXAMPLE 3B illustrates the reaction of dimethyl sulfate and 1,1-dimethylhydrazine to form the methosulfate of 1,1,1-trimethylhydrazine which is used without isolation for the conversion of picramide to TATB. Alkylation of a 1,1-diakylhydrazine with dimethyl sulfate to give a 1,1,1-trialkylhydrazine methosulfate is described by O. Westphal, *Chem. Ber.*, vol. 74, pp. 1365–1372 (1941).

The extent of the amination of carbocyclic aromatic compounds or heterocyclic aromatic compounds using the 1,1,1-trialkylhydrazinium salt is normally controlled by one of skill in the art by judicious choice of temperature, time, solvents, strong base and amount of 1,1,1-trialkylhydrazinium salt. Alcohol solvents usually limit the reaction to production of nitroaromatic compounds, such as DATB and picramide, because alcohols appear to slow or stop complete amination. The amount of reagent is also important to produce DATB, i.e. between about 1.9 and 2.3 molar equivalents per mole of structure V, preferably about 2.1 eq.

Solvents—In the present invention, solvents which are preferred include aliphatic alcohols having 1–6 carbon atoms (all isomers), cycloalkyl alcohols having 1–6 carbon atoms and the like. Useful dipolar aprotic solvents include, dimethylsulphoxide, N-methylpyrrolidone, hexamethylphosphoramide, dimethylformamide, diethylformamide, dimethylacetamide and the like. The solvent may also include diluents (benzene, chloroform) as needed to optimize conditions and product yields. Mixtures of solvents are also claimed.

Strong Bases—In the present invention, strong bases are usually the alkali metal salts of alcohols. Alcohols having 1–15 carbon atoms are preferred, more preferred are alcohols having 1–10 carbon atoms, and most preferably are alcohols having 1–6 carbon atoms. Especially preferred alcohols include methanol, ethanol, propanol, (n- or iso-) and butanol (n-, iso-, sec-, or tert-).

Other bases employed in VNS aminations include 1,1,3, 3-tetramethylguanidine, sodium hydroxide and sodium dimsylate. TMHI reacts with picramide in the presence of 1,1,3,3-tetramethylguanidine to provide DATB (see EXAMPLE 2A). In contrast, sodium hydroxide (see EXAMPLE 3C) and sodium dimsylate (see EXAMPLE 3D) promote TATB production when used as bases in the reaction of picramide and TMHI.

This methodology is extended to the introduction of alkyl- or aryl-substituted amines to electrophilic aromatic and heteroaromatic rings. This may be accomplished by reaction of the electrophilic aromatic ring with a 1,1-dialkyl-1,2-di-R (R=alkyl or aryl) hydrazinium salt in DMSO in the presence of base.

The 1,1-dialkyl-1,2-di-R (R=alkyl or aryl) hydrazinium salt is synthesized by two general methods:

1. The reaction of a symmetrical hydrazine bearing an alkyl or aryl radical with methyl iodide produces a 1,1-dimethyl-1,2-dialkyl (or aryl) hydrazinium iodide. The identity of the substituted amine which is transferred in the VNS reaction is determined by the selection of the R- group on the symmetrical hydrazine starting material.

Therefore:

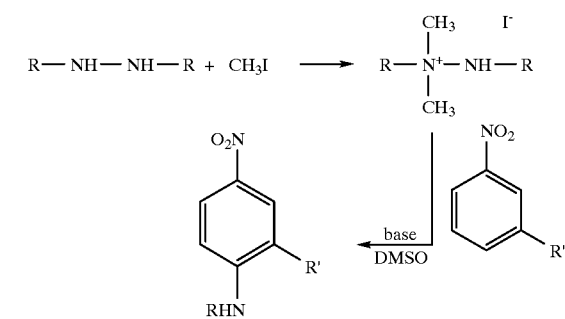

(see O. Westphal, *Chem. Ber.*, (1941), 1362).

2. The reaction of a trialkylhydrazinium salt with an alkyl or acyl halide in the presence of base yields a 1,1,1-trialkyl-2-(R)-hydrazinium halide or the corresponding ylide. Therefore:

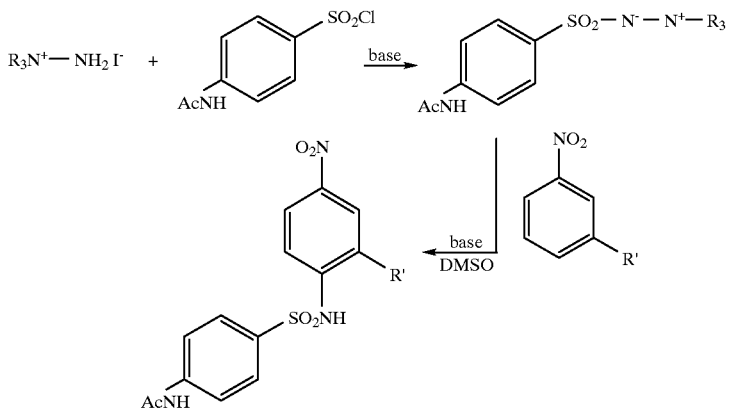

(see J. N. Ashley, et al., *J. Chemical Soc.*, (1947), p. 60).

The VNS reaction is applied to substituted aromatics bearing at least one electron-withdrawing group, e.g., a nitro-group. The aromatics include heterocycles such as substituted and unsubstituted pyridine, pyrimidine, pyrazine, quinoline, quinoxaline, imidazole, triazole and pyrazole.

The use of 1,1,1-triakylhydrazinium salts and 1,1-dialkyl-1,2-di-R (R=alkyl or aryl) hydrazinium salts, e.g., halides as VNS reagents to add amino-groups to electrophilic aromatic rings have not yet been described. The general utility of these reagents to add amino groups to electrophilic aromatic compounds is also claimed.

3. This methodology is extended to synthesis of polymeric VNS reagents for the introduction of amino groups onto electrophilic aromatic rings. Thus, chloromethyl-substituted polystyrene is reacted with 1,1-dimethylhydrazine to yield a polymeric 1,1,1-trialkylhydrazinium chloride which is used in VNS reactions to introduce amino-groups onto electrophilic aromatic rings.

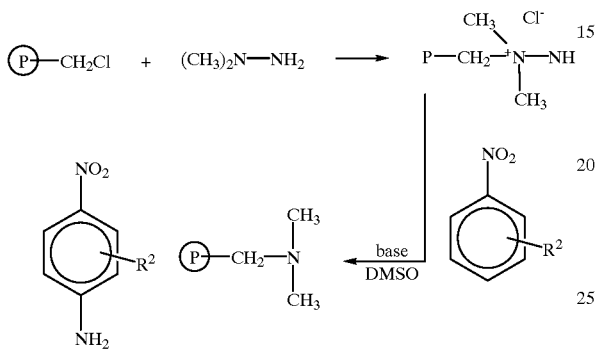

The spent polymeric VNS reagent is then regenerated by reaction with chloramine.

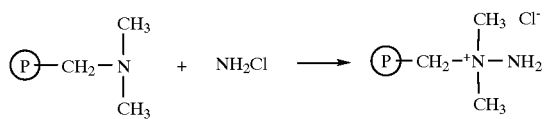

(see G. M. Omietanski, et al., *J. Chemical Society*, (1956), p. 1211–13).

In the present invention, the starting material, e.g. trinitrated benzene structure is contacted with strong base in the presence of one or more solvents at between about 0 and 50° C. and ambient pressure for between about 0.1 and 24 hr, preferably between about 1 and 12 hr, more preferably between about 1 and 5 hr. Preferably, the temperature is between about 10 and 30° C., and more preferably about ambient temperature (i.e. about 20° C.). The trinitrated aromatic compound is reacted with ATA.

The extent of the amination using 4-amino-1,2,4-triazole is normally controlled by one of skill in the art by judicious choice of temperature, time, solvents, strong base and amount of ATA. The amount of ATA reagent is also important to produce DATB, i.e. between about 1.9 and 2.3 molar equivalents per mole of structure V, preferably about 2.1 eq.

Hydroxylamine and its O-alkyl derivatives are also used to replace a stoichiometrically equivalent amount of ATA, and these reagents produce primarily DATB.

Picramide reacts with hydroxylamine (see EXAMPLE 9 below) and its O-alkyl derivatives (see EXAMPLES 10 and 11 below) in the presence of strong base and dipolar aprotic solvents to produce DATB when the reaction is run at ambient temperature. Seko, U.S. Pat. No. 5,466,871, Nov. 14, 1995 independently verified that O-alkylhydroxylamines mono-aminate substituted nitroarenes to produce a mixture of o- and p-nitroanilines in the presence of strong base and dipolar aprotic solvents at ambient temperatures. Seko and Kawamura (J. Org. Chem., Vol. 61, pp. 442–443 (1996)) also report that unsubstituted hydroxylamine will not aminate nitrobenzene (see their Table 1, entry 6: the starting material was recovered quantitatively) while a variety of O-alkylhydroxylamines efficiently mono-aminate nitrobenzene (see their Table 1, entries 1–5) under basic conditions at room temperature. We reinvestigated the use of hydroxylamine (a cheap commodity chemical) as a nucleophilic aminating agent in spite of the poor reactivity was reported by Seko (vide stipra). Surprisingly, we found that hydroxylamine (generated in situ from hydroxylamine hydrochloride and base) will diaminate picramide at elevated temperature (90° C.) to furnish TATB as described in EXAMPLE 9A below.

In the present invention, the startina material, an electrophic aromatic compound, such as a trinitrated benzene structure, is contacted with strong base in the presence of one or more solvents at between about 0 and 50° C. and ambient pressure for between about 0.1 and 24 hr, preferably between about 1 and 12 hr, more preferably between about 1 and 5 hr. Preferably, the temperature is between about 10 and 30° C., and more preferably about ambient temperature (i.e. about 20° C.). The electrophilic aromatic compound is reacted with ATA.

A. Katritzky et al., *Journal of Organic Chemistry*, vol. 51, pp. 5039–5040 (1986) disclose the use of 4-amino-1,2,4-triazole (ATA) for direct mono-amination of a substituted mononitrobenzene. There is no teaching or suagestion to use ATA for the multiple amination of nitro benzenes having two or more nitro substituents.

The extent of the amination using 1-amino-1,2,4-triazole is normally controlled by judicious choice of temperature, time, solvents, stronc, base and amount of ATA. The amount of ATA reagent is also important to produce DATB, i.e. between about 1.9 and 2.3 molar equivalents per mole of structure V, preferably about 2.1 eq.

Hydroxylamine and its O-alkyl derivatives are also used to replace a stoichiometrically equivalent amount of ATA, and they produce primarily DATB.

Aromatic structures produced by the present invention include, but are not limited to:

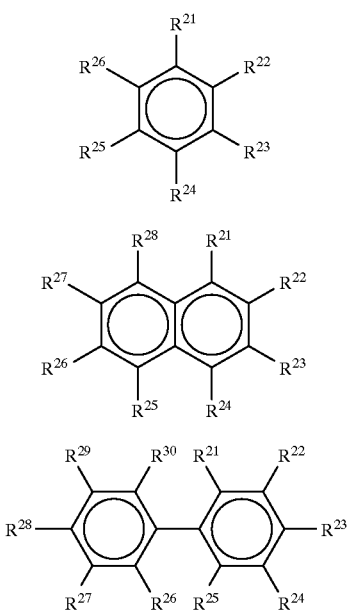

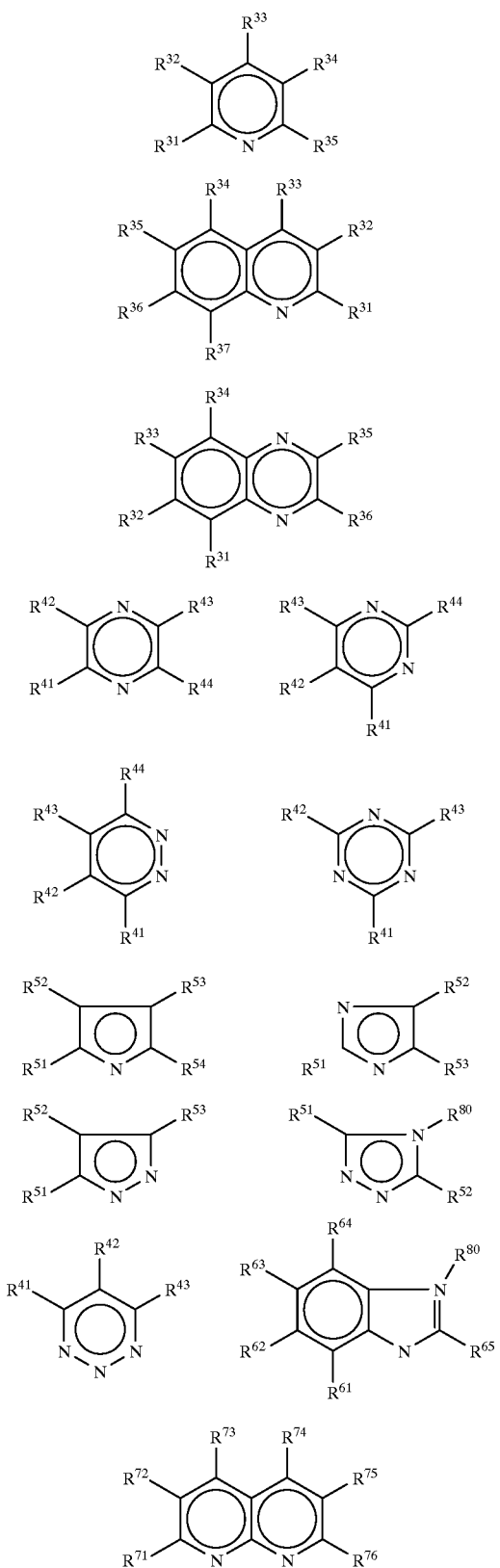

for benzene at least one of $R^{21}$ to $R^{26}$ is an electron withdrawing group, and at one of $R^{21}$ to $R^{26}$ is an amino group;

for pyridine at least one of $R^{31}$ to $R^{35}$ is an electron withdrawing group, and of $R^{31}$ to $R^{35}$ is an amino group; and for naphthalene, at least one of $R^{21}$ to $R^{28}$ is an electron withdrawing group, and at least one of $R^{21}$ to $R^{28}$ is an amino group;

for biphenyl, at least one of $R^{21}$ to $R^{30}$ is an electron withdrawing group, and at least one on one of $R^{21}$ to $R^{30}$ is amine, an amino group;

for quinoline, at least one of $R^{31}$ to $R^{37}$ is an electron withdrawing group, and at least one of $R^{31}$ to $R^{37}$ is an amino group;

for 1,4-quinoxaline at least one of $R^{31}$ to $R^{36}$ is an electron withdrawing group, and at least one of $R^{31}$ to $R^{36}$ is an amino group;

for the diamino six-membered rings, at least one of $R^{41}$ to $R^{44}$ is an electron withdrawing group, and at least one of $R^{41}$ to $R^{44}$ is an amino group;

for the six-membered rings containing three nitrogen atoms, at least one of $R^{41}$ to $R^{43}$ is an electron withdrawing group, and at least one on $R^{41}$ to $R^{43}$ is an amino group; and for the five-membered heterocyclic rings containing one, two, or three nitrogens, at least one of $R^{51}$ to $R^{54}$ is an electron withdrawing group, and at lest one of $R^{51}$ to $R^{54}$ is an amino group, for indole at lest one of $R^{61}$ to $R^{65}$ is an electron withdrawing group, and at least one of $R^{61}$ to $R^{65}$ is an amino group;

for fused pyridine have two six-membered rings, at least one of $R^{71}$ to $R^{76}$ is an electron withdrawing group, and at least one of $R^{11}$ to $R^{76}$ is an amino group;

wherein $R^{80}$ is alkyl having 1 to 6 carbon atoms;

wherein the electron withdrawing group is selected from —CN, —NO$_2$, —COR, —CO$_2$R$_1$, —CONR$_2$, —SO$_2$R, —SO$_3$H, —CF$_3$, —F, —Cl, —Br, 13 I and —NH$_2$, where R$_1$ and R$_2$ are C$^1$ to C$^6$ alkyl.

Other substituents may be selected from either electron-withdrawing or electron-donating substituents and may be selected from but not restricted to the following: —NO$_2$, —CN, —CO$_2$R, —SO$_2$R, —CF$_3$, —F, —Cl, —Br, —I, —COR, —CONR$_2$, —OR, —SR, -alky, -aryl, -heteromatic, —SO$_3$H.

If the electrophilic aromatic compound contains more than one electron withdrawing group, then the number of amino groups which may be added to the ring may equal the number of electron withdrawing groups.

Solvents—In the present invention, solvents which are preferred include dipolar aprotic solvents including, but not limited to, dimethylsulphoxide N-methylpyrrolidone, hexamethylphosphoramide, dimethylformamide, diethylformamide, dimethylacetamide and the like. The solvent may also include diluents (benzene, chloroform) as needed to optimize conditions and product yields. Mixtures of solvents are also included.

General

Picramide is obtained from commercial sources or prepared according to E. Y. Spencer et al., *Canadian Journal Research*, vol. 24B, pp. 204–207 (1946).

1,3,5-Trinitrobenzene is obtained from commercial sources or prepared according to *Organic Synthesis.*

2,4,6-Trinitrotoluene is obtained from commercial sources or is prepared according to any literature source.

DMSO is dried and stored over 4A molecular sieves.

4-Amino-1,2,4-triazole (ATA) is commercially available from Reilly Industries, Inc., 1500 South Tibbs Avenue, Indianapolis, Ind. 46242-0912.

The reactions were performed in TEFLON® capped reaction vessels or reaction vessels equipped with drying tubes containing anhydrous calcium sulfate to protect VNS reactions from atmospheric moisture.

The following Examples are to explain and describe the invention. They are not to be construed to be limiting in any way.

EXAMPLE 1

Preparation of 1,1,1-Trimethylhydrazinium Iodide (TMHI)

(a) 1,1-Dimethylhydrazine (5.1 ml, 67 mmol) is dissolved in 60 ml of tetrahydrofuran (THF). Methyl iodide (4 ml, 67 mmol) is added with ice-bath cooling and mechanical stirring. The resulting slurry is diluted with THF to facilitate stirring. The reaction mixture is stirred at ambient temperature for 2 hr, and a white solid is collected by filtration. Recrystallisation from ethanol (100 ml) yields 11.6 g of TMHI (86%) as white plates; m.p. 230–232° C. (softening at 223° C.); $^1$H-nmr ($D_2O$) δ 3.42 (—$CH_3$), 4.55 ppm ($NH_2$ exchangeable).

(b) Similarly, Example 1(a) is repeated except that 1,1-dimethylhydrazine is replaced by a stoichiometrically equivalent amount of 1,2-di-R (where R=alkyl or aryl) hydrazine and a similar amount of 1,1,-dimethyl-1,2-di-R-hydrazinium iodide is produced.

(c) Similarly, when Example 1(a) is repeated except that methiodide is replaced by a stoichiometrically equivalent amount of ethyl chloride and reacted with 1,1-diethylhydrazine to produce a similar amount of 1,1,1-triethylhydrazinium chloride.

EXAMPLE 2

Preparation of DATB From Picramide (a) Picramide (0.30 g, 1.3 mmol) and TMHI (0.56 g, 2.8 mmol) are dissolved in 10 ml of dry dimethylsulphoxide (DMSO) with protection from atmospheric moisture. Sodium methoxide (0.31 g, 5.7 mmol) is added in one portion with stirring and the resulting red slurry is stirred at ambient temperature for 3 hr. The reaction mixture is poured into ice water (25 ml) and acidified to pH 4 with hydrochloric acid. The product is collected by filtration, washed with water and dried to yield 0.24 g (75%) of beige-yellow solid. The IR spectra for this material and a reference sample of DATB are identical.

(b) Similarly, Example 2(a) is repeated except that 1,1,1-trimethylhydrazinium iodide is replaced by a stoichiometrically equivalent amount of 1,1,1-triethylhydrazinium chloride, and a similar amount of DATB is produced.

(c) Similarly, when Example 2(a) is repeated except that DMSO is replaced by a volumetrically equivalent amount of methanol, ethanol n-propanol, iso-propanol or normal butanol, and the base is sodium methoxide, sodium ethoxide, sodium n-propoxide, sodium isopropoxide, or potassium tert-butoxide, a mixture of picramide and DATB is produced. The DATB is purified by crystallization from DMF or DMSO.

EXAMPLE 2A

Preparation of DATB From Picramide Using TMHI and 1,1,3,3-Tetramethylguanidine (a) Picramide (0.228 g, 1.00 mmol) and TMHI (1.01 g, 5.00 mmol) are dissolved in 10 ml of dry DMSO. 1,1,3,3-Tetramethylguanidine (2.10 ml, 11.1 mmol) is added and the deep red suspension is stirred and heated from ambient temperature to 90° C. over a 1 hr period. The reaction suspension is stirred an additional 14 hr at 90° C. and cooled to ambient temperature. The reaction is quenched in 30 ml of cold, aqueous 0.6M hydrochloric acid to yield a suspension. The suspension is centrifuged and the collected residue is washed with water (4×30 ml) and acetone (2×30 ml). Vacuum drying yields 0.107 g of an orange solid (44%) with an IR spectrum identical to that for known DATB.

EXAMPLE 3

Preparation of TATB From Picramide (a) Picramide (1.00 g, 4.38 mmol) and TMHI (3.54 g, 17.5 mmol) are dissolved in dry DMSO (34 ml). Sodium methoxide (1.89 g, 35.0 mmol) is added in one portion and the resulting red slurry is stirred for 16 hr at ambient temperature under a dry atmosphere. The reaction mixture is poured into ice water and acidified to pH 4 with concentrated hydrochloric acid. The resulting precipitate is collected, and washed with water (20 ml) and acetone (10 ml) to yield 1.07 g (95%) of beige-yellow powder; m.p. 355° C. with decomposition. The IR spectra for this material and TATB are identical.

(b) Similarly, Example 3(a) is repeated except that 1,1,1-trimethylhydrazinium iodide is replaced by a stoichiometrically equivalent amount of 1,1,1-triethylhydrazinium chloride, and a similar amount of TATB is produced.

(c) Similarly, when Example 3(a) is repeated except that DMSO is replaced by a volumetrically equivalent amount of DMF, or DMAC, and sodium methoxide is replaced by a stoichiometrically equivalent amount of sodium ethoxide, sodium n-propoxide, sodium isopropoxide, or potassium tert-butoxide respectively, a similar amount of TATB is produced.

EXAMPLE 3A

In Situ Preparation of 1,1,1-Trimethylhydrazinium Iodide (TMHI) and Subsequent Use in Preparation of TATB From Picramide (a) Methyl iodide (0.31 ml, 5.0 mmol) is added to a solution of 1,1-dimethylhydrazine (0.38 ml, 5.0 mmol) dissolved in 7.5 ml of dry DMSO. The solution is stirred for 0.5 hr. Picramide (0.23 g, 1.0 mmol) and sodium methoxide (0.60 g, 11 mmol) are added and the resulting brown suspension is stirred at ambient temperature for 16.5 hr. A 0.75 ml sample (10% of reaction volume) is removed, treated with cold water (4 ml) centrifuged. The resulting residue is washed with water and vacuum-dried. IR analysis establishes the sample as TATB and the absence of DATB. The remaining reaction suspension (90%) is stirred an additional 23.5 hr and quenched with citric acid monohydrate (1.05 g, 5.0 mmol). The resulting slurry is diluted with DMSO (10 ml) to facilitate stirring. The suspension is filtered and the collected residue is washed with DMSO (2×5 ml) and hot water (4×10 ml). Vacuum drying yields 0.21 g of a yellow solid (91%) with an IR spectrum identical to that for known TATB.

EXAMPLE 3B

In Situ Preparation of 1,1,1-Trimethylhydrazinium Methosulfate and Subsequent Use in Preparation of TATB From Picramide (a) Dimethyl sulfate (0.47 ml, 5.0 mmol) is added to a solution of 1,1-dimethylhydrazine (0.38 ml, 5.0 mmol)

dissolved in 10 ml of dry DMSO. The solution is stirred for 2.5 hr at ambient temperature. Picramide (0.23 g, 1.0 mmol) and sodium ethoxide (1.14 g, 17 mmol) are added and the resulting red suspension is stirred at ambient temperature for 0.1 hr and then heated and stirred at 90° C. for 12 hr. The reaction suspension is cooled to ambient temperature and quenched with citric acid monohydrate (1.05 g, 5.0 mmol). The resulting slurry is diluted with DMSO (10 ml) to facilitate stirring. The suspension is centrifuged and the resulting residue is washed with water (4×30 ml). Vacuum drying yields 0.16 g of a deep yellow solid (56%) with an IR spectrum identical to that for known TATB.

EXAMPLE 3C

Preparation of TATB From Picramide Using TMHI and Sodium Hydroxide (a) Picramide (0.228 g, 1.00 mmol) and TMHI (1.01 g, 5.00 mmol) are dissolved in 7.5 ml of dry DMSO. Addition of 0.58 ml (11 mmol) of 50% aqueous sodium hydroxide gives an intense red suspension which is stirred at ambient temperature for 0.1 hr and at 90° C. for 14 hr. The reaction suspension is cooled to ambient temperature (about 20° C.) and quenched with citric acid monohydrate (1.05 g, 5.0 mmol). The slurry is centrifuged and the resulting residue is washed with water (4×30 ml). Vacuum drying yields 0.056 g of a deep yellow solid (22%) with an IR spectrum identical to that for known TATB.

EXAMPLE 3D

Preparation of TATB From Picramide Using TMHI and Sodium Dimsylate (a) A 60% dispersion of sodium hydride in mineral oil (0.443 g, 11.1 mmol) is added to 7.5 ml of dry DMSO and stirred at 70° C. under argon for 1 hr. The resulting solution of sodium dimsylate in DMSO is cooled to ambient temperature. TMHI (1.01 g, 5.00 mmol) and picramide (0.228 g, 1.00 mmol) are added and the resulting suspension is stirred at ambient temperature (6 hr) and then at 70° C. (15 hr). The suspension is cooled to ambient temperature and quenched with aqueous citric acid monohydrate (1.05 g, 5.0 mmol). The suspension is filtered (0.2 micron pore) and the collected residue is washed with DMSO, petroleum ether (bp 30–70° C.) and water. Vacuum drying yields 0.109 g (42%) of TATB.

EXAMPLE 4

Preparation of DATB From TNB (a) DMSO (5 ml) is added with rapid stirring to a mixture of TNB (0.148 g, 0.695 mmol), TMHI (1.03 g, 5.10 mmol) and sodium methoxide (0.609 g, 11.3 mmol). The dark brown suspension is stirred at ambient temperature for 2 hr. The reaction mixture is poured into cold 0.12N aqueous HCl (200 ml). The resulting precipitate is collected, washed with water and dried to give 0.148 g (61%) of a dark orange solid. The IR spectra for this material and DATB are identical.

(b) Similarly, Example 4(a) is repeated except that 1,1,1-trimethylhydrazinium iodide is replaced by a stoichiometrically equivalent amount of 1,1,1-triethylhydrazinium chloride, and a similar amount of DATB is produced.

(c) Similarly, when Example 4(a) is repeated except that DMSO is replaced by a volumetrically equivalent amount of DMF or DMAC and sodium methoxide is replaced by a stoichiometrically equivalent amount of sodium ethoxide, sodium n-propoxide, sodium isopropoxide, or sodium tert-butoxide respectively, a mixture of picramide and DATB is produced. The DATB is purified by crystallization from DMF and DMSO.

EXAMPLE 5

Preparation of TATB From TNB (a) TNB (0.148 g, 0.693 mmol) and TMHI (1.03 g, 5.10 mmol) are dissolved in DMSO (10 ml) prior to the addition of sodium methoxide (0.600 g, 11.1 mmol). The dark brown suspension is stirred for 20 hr at ambient temperature. The reaction mixture is poured into cold 0.12N aqueous HCl (200 ml). The resulting precipitate is washed with water and dried to give 0.158 g (61%) of a light brown powder having the IR spectrum of TATB.

(b) Similarly, Example 5(a) is repeated except that 1,1,1-trimethylhydrazinium iodide is replaced by a stoichiometrically equivalent amount of 1,1,1-triethylhydrazinium chloride, and a similar amount of TATB is produced.

(c) Similarly, when Example 5(a) is repeated except that DMSO is replaced by a volumetrically equivalent amount of DMF, DMAC, and sodium methoxide is replaced by a stoichiometrically equivalent amount of sodium ethoxide, sodium n-propoxide, sodium isopropoxide, or potassium tert-butoxide respectively, a similar amount of TATB is produced.

EXAMPLE 6

Preparation of Nitroanilines From Nitrobenzene (a) Nitrobenzene (0.133 ml, 1.29 mmol) and TMHI (0.283 g, 1.40 mmol) are dissolved in 7 ml DMSO. Potassium tert-butoxide (0.348 g, 3.10 mmol) is added in one portion and the resulting dark red-orange solution is stirred for 4 hr at ambient temperature. The reaction mixture is poured over 5 g ice, acidified with 10% hydrochloric acid and stirred for 0.5 hr. The resulting solution is extracted with ethyl acetate (3×20 ml). The combined organic layers are washed with water, dried (MgSO$_4$) and evaporated. The resulting brown solid is chromatographed using silica gel eluted with, 9:1 petroleum ether-acetone to yield 0.096 g o-nitroaniline and 0.062 g p-nitroaniline (0.158 g total, 86% overall yield) in the relative isomer ratio of 61:39.

(b) Similarly, Example 6(a) is repeated except that 1,1,1-trimethylhydrazinium iodide is replaced by a stoichiometrically equivalent amount of 1,1,1-triethylhydrazinium chloride, and a similar amount of nitroanilines are produced.

(c) Similarly, when Example 6(a) is repeated except that DMSO is replaced by a volumetrically equivalent amount of DMF or DMAC, and potassium tert-butoxide is replaced by a stoichiometrically equivalent amount of sodium methoxide, sodium ethoxide, sodium n-propoxide, sodium isopropoxide, or sodium tert-butoxide respectively, a similar amount of nitroanilines are produced.

EXAMPLE 7

Amination of 3-Substituted Nitrobenzenes With TMHI

TMHI is reacted with the same 3- substituted nitrobenzene substrates used with 4-amino-1,2,4-triazole (ATA) as reported by A. R. Katritzky and K. S. Laurenzo, *Journal of Organic Chemistry*, vol. 51, pp. 5039–5040 (1986). The nitroaromatic substrate (1.3 mmol) and TMHI (1.4–1.9 mmol) are dissolved in dry DMSO (7 ml), and solid alkoxide (sodium methoxide or potassium tert-butoxide) is added with stirring. The solution immediately becomes nearly black in color. After 4–17 hr of stirring at room temperature, the reaction is quenched with 10% HCl. Precipitated solids are collected by filtration and washed with cold water. The filtrate is extracted with ethyl acetate and the crude products obtained upon evaporation of the solvent are subjected to chromatography on silica. The identity of all products is confirmed by comparison of melting points and/or $^1$H NMR with authentic standards. The results are summarized in Table I.

Table I shows that TMHI is not as selective as ATA, producing in most cases multiple regioisomeric products. TMHI displays a tendency to aminate in the 2-position which contrasts with exclusive 4-amination in the case of ATA. The very high reactivity of TMHI is of interest and with m-dinitrobenzene diamination takes place even under stoichiometric conditions.

TABLE 1

Amination of 3-Substituted Nitrobenzenes

| compd | R | % yield | a | b | c |
|---|---|---|---|---|---|
| 2 | H | 85 | 61 | 39 | (na) |
| 3 | CH$_3$ | 84 | 38 | 35 | 27 |
| 4 | Cl | 82 | 32 | 49 | 19 |
| 5 | COOH | 95 | 0 | 71 | 29 |
| 6 | OCH$_3$ | 66 | 90 | 10 | 0 |
| 7 | F | 84 | 45 | 47 | 8 |
| 8 | I | 76 | 45 | 38 | 17 |
| 9 | CN | 41 | 20 | 44 | 36 | isomer ratios shown above columns a, b, c.

EXAMPLE 8

Preparation of Diamino-TNT (DATNT) From TNT (a) TNT (0.227 g, 1.00 mmol) and TMHI (1.03 g, 5.10 mmol) are dissolved in DMSO (10 ml). Sodium methoxide (0.600 g, 11.1 mmol) is added in one portion with stirring. The dark brown suspension is stirred for 23 hr at ambient temperature. The reaction mixture is poured into cold 0.12N aqueous HCl (200 ml) and stirred for 20 minutes prior to the collection of precipitate. The product is washed with water and dried to give 0.212 g (82%) of DATNT as a dark, olive green solid; $^1$H-nmr (DMSO -d$_6$) δ 8.08 (br s, 4, NH$_2$) and 2.18 (s,3,ArCH$_3$).

(b) Similarly, Example 8(a) is repeated except that 1,1,1-trimethylhydrazinium iodide is replaced by a stoichiometrically equivalent amount of 1,1,1-triethylhydrazinium chloride, and a similar amount of DATNT is produced.

(c) Similarly, when Example 5(a) is repeated except that DMSO is replaced by a volumetrically equivalent amount of DMF or DMAC, and sodium methoxide is replaced by a stoichiometrically equivalent amount of sodium ethoxide, sodium n-propoxide, sodium isopropoxide, or potassium tert-butoxide respectively, a similar amount of DATNT is produced.

EXAMPLE 9

Preparation of DATB From Picramide Using Hydroxylamine (a) Hydroxylamine hydrochloride (0.709 g, 10.2 mmol) and picramide (0.477 g, 2.09 mmol) are dissolved in 17 ml DMSO. Sodium methoxide (1.28 g, 23.6 mmol) in methanol (5.40 ml) is added with stirring, and the resulting brown suspension is stirred at ambient temperature for 4 hr. The reaction mixture is poured into 200 ml of saturated aqueous ammonium chloride. The product is collected by filtration, washed with water and cold acetone to yield 0.139 g (27%) of a yellow solid. The IR spectra for this material and DATB are identical.

(b) Similarly, when Example 9(a) is repeated except that methanol is replaced by a volumetrically equivalent amount of ethanol, n-propanol, iso-propanol or tert-butanol, and sodium methoxide is replaced by a stoichiometrically equivalent amount of sodium ethoxide, sodium n-propoxide, sodium isopropoxide, or sodium tert-butoxide respectively, a similar amount of DATB is produced.

EXAMPLE 9A

Preparation of TATB From Picramide Using Hydroxylamine at Elevated Temperature (a) Picramide (0.228 g, 1.00 mmol) and hydroxylamine hydrochloride (0.348 g, 5.00 mmol) are dissolved in 10 ml DMSO. Sodium ethoxide (1.10 g, 16.1 mmol) is added with stirring. The resulting brown suspension is stirred and heated from ambient temperature to 90° C. over the course of 1 hr. Stirring and heating (90° C.) are continued for an additional 12.5 hr. The reaction suspension is cooled to ambient temperature and quenched with citric acid monohydrate (1.05 g, 5.0 mmol). The suspension is centrifuged and the resulting residue is washed with water (4×30 ml). Vacuum drying yields 0.191 g of a light greenish-yellow solid (74%) with an IR spectrum corresponding to that for known TATB.

EXAMPLE 10

Preparation of DATB From Picramide Using O-Methylhydroxylamine (a) DMSO (10 ml) is added with rapid stirring to a mixture of picramide (0.477 g, 2.09 mmol), O-methylhydroxylamine hydrochloride (0.709 g, 10.2 mmol) and sodium methoxide (1.27 g, 23.6 mmol). The dark brown suspension is stirred at ambient temperature for 2 hr. The reaction mixture is poured into cold 0.12N aqueous HCl (200 ml). The resulting precipitate is collected, washed with water and dried to yield 0.454 g (89%) of a yellow solid. The IR spectra for this material and DATB are identical.

(b) Similarly, when Example 10(a) is repeated except that sodium methoxide is replaced by a stoichiometrically equivalent amount of sodium ethoxide, sodium n-propoxide, sodium isopropoxide, or potassium tert-butoxide respectively, a similar amount of DATB is produced.

EXAMPLE 11

Preparation of DATB From Picramide Using O-Benzylhydroxylamine (a) DMSO (15 ml) is added with rapid stirring to a mixture of picramide (0.477 g, 2.09 mmol), O-benzylhydroxylamine (1.64 g, 10.3 mmol) and sodium methoxide (1.91 g, 35.4 mmol). The brown suspension is stirred at ambient temperature for 15 hr. The reaction mixture is poured into cold 0.12N aqueous HCl (200 ml). The resulting precipitate is collected, washed with water and dried to yield 0.444 g (87%) of DATB.

(b) Similarly, when Example 11 (a) is repeated except sodium methoxide is replaced by a stoichiometrically equivalent amount of sodium ethoxide, sodium n-propoxide, sodium isopropoxide, or potassium tert-butoxide respectively, a similar amount of DATB is produced.

EXAMPLE 12

Preparation of TATB From TNB Using ATA (a) A suspension of sodium methoxide (1.19 g, 22.2 mmol) in DMSO (15 ml) is added to a solution of TNB (0.296 g, 1.39 mmol) and ATA (0.853 g, 10.2 mmol) in 4 ml DMSO with rapid stirring. The brown suspension is stirred for 2 hr at ambient temperature. The reaction mixture is poured into cold 0.12N aqueous HCl (200 ml). The resulting precipitate is collected, washed with water and dried to yield 0.353 g (98%) of a yellow solid. The IR spectra for this material and TATB are identical.

(b) Similarly, when Example 12(a) is repeated except sodium methoxide is replaced by a stoichiometrically equivalent amount of sodium ethoxide, sodium n-propoxide, sodium isopropoxide, or potassium tert-butoxide respectively, a similar amount of TATB is produced.

EXAMPLE 13

Preparation of TATB From DATB Using ATA (a) Sodium methoxide (0.600 g, 11.1 mmol) is added to a solution of DATB (0.25 g, 1.05 mmol) and ATA (0.429 g, 5.10 mmol) in 15 ml DMSO. The reddish brown suspension is stirred for 2.5 hr at ambient temperature. The reaction mixture is poured into cold 0.12N aqueous HCl (200 ml). The resulting precipitate is collected, washed with water and dried to yield 0.270 g (100%) of TATB.

(b) Similarly, when Example 13(a) is repeated except sodium methoxide is replaced by a stoichiometrically equivalent amount of sodium ethoxide, sodium n-propoxide, sodium isopropoxide, or potassium tert-butoxide respectively, a similar amount of TATB is produced.

EXAMPLE 14

Preparation of TATB From Picramide Using ATA (a) Sodium methoxide (1.19 g, 22.0 mmol) is added to a solution of picramide (0.228 g, 1.00 mmol) and ATA (0.841 g, 10.0 mmol) in 15 ml DMSO. The reddish orange suspension is stirred for 3 hr at ambient temperature. The reaction mixture is poured into cold 0.12N aqueous HCl. The resulting precipitate is collected, washed with water and dried to yield 0.236 g (91%) of TATB.

(b) Similarly, when Example 14(a) is repeated except sodium methoxide is replaced by a stoichiometrically equivalent amount of sodium ethoxide, sodium n-propoxide, sodium isopropoxide, or potassium tert-butoxide respectively, a similar amount of TATB is produced.

EXAMPLE 15

Preparation of Diamino-TNT (DATNT) From TNT (a) A suspension of sodium methoxide (1.19 g, 22.2 mmol) in 13 ml DMSO is added to a solution of TNT (0.476 g, 2.10 mmol) and ATA (0.853 g, 10.2 mmol) in 4 ml DMSO. The brown suspension is stirred for 3 hr at ambient temperature and then poured into a saturated aqueous solution of ammonium chloride (200 ml). A deep yellow solid is collected, washed with water and dried to give 0.337 g (62%) of DATNT: $^1$H-nmr (CDCl$_3$+DMSO-d$_6$) δ 8.44 (br, s, 4, NH$_2$) and 2.35 (s, 3, ArCH$_3$).

(b) Similarly, when Example 15(a) is repeated except sodium methoxide is replaced by a stoichiometrically equivalent amount of sodium ethoxide, sodium n-propoxide, sodium isopropoxide, or potassium tert-butoxide respectively, a similar amount of DATNT is produced.

EXAMPLE 16

Synthesis of Animoheterocyclic Compounds (a) Example 2(a) is repeated except that the picramide is replaced by a stoicheometrically equivalent amount of mononitro- or dinitro-pyridine. The corresponding monoamino and diamino nitro pyridine is produced.

(b) Example 2(a) is repeated except that the picramide is replaced by a stoicheometrically equivalent amount of mononitro or dinitropyrazole and the corresponding monoamino and diamino-nitropyrazole is produced.

While only a few embodiments of the present invention have been shown and described herein, it is apparent to those skilled in the art that various modifications and changes can be made in these novel vicarious nucleophilic substitution processes of monoamination and/or polyamination of electrophilic aromatic compounds, using for example hydroxylamine, 1,1,1-trialkyl hydrazinium salts or 4-amino-1,2,4-triazole to produce amine compounds, such as DATB or TATB, without departing from the spirit and scope of the present invention. All such modifications and changes coming within the scope of the appended claims are intended to be covered thereby.

We claim:

1. A process to produce a mono amino, diamino or polyamino aromatic compound, which process comprises:

(a) reacting at ambient pressure and a temperature of between about 0 and 50° C. for between about 0.1 and 24 hr, an electrophilic aromatic compound:

(V)

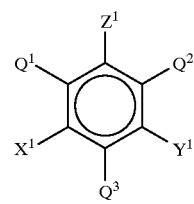

wherein $Q^1$, $Q^2$, $Q^3$, X, Y, and Z are each independently selected from the group consisting of —CN, —NO$_2$, —COR, —CO$_2$R$_1$, —CONR$_2$, —SO$_2$R, —SO$_3$H, —CF$_3$, —F, —Cl, —Br, —I and —NH$_2$, wherein R, R$_1$, and R are independently selected from the group consisting of alkyl having one to six carbon atoms, with the proviso that at least one of Q$^1$, Q$^2$, Q$^3$, X$^1$, Y$^1$, and Z$^1$ is hydrogen, with an effective amount of reagent selected from:
  (i) 1,1,1,-trialkylhydrazinium salt wherein alkyl is selected from the group consisting of methyl, ethyl, propyl, butyl and benzyl and the anion is selected from the group consisting of chloride, bromide, iodide, fluoride, sulfate, hydroxide, mesylate, triflate, and tetrafluoroborate,
  (ii) hydroxylamine,
  (iii) O-alkyl hydroxyl amine where alkyl is C$_1$ to C$_{10}$ carbon atoms, or
  (iv) 4-amino-1,2,4-triazole; and combinations thereof, in the presence of tetraalkyl guanidine wherein alkyl is C$_1$ to C$_{10}$;
  or the presence of a strong base selected from the group consisting of sodium butoxide, potassium butoxide, potassium propoxide, sodium propoxide, sodium ethoxide, potassium ethoxide, sodium methoxide, potassium methoxide, and combinations thereof;
   in a solvent selected from the group consisting of methanol, ethanol, propanol, butanol, dimethylsulphoxide, N-methylpyrrolidone, hexamethylphosphoramide, dimethylformamide, dimethylacetamide and mixtures thereof, provided that when alcohols are present primarily DATB and picramide are formed; and (b) isolating the monoamino, diamino or polyamino aromatic compound produced.

2. A process to produce a mono amino, diamino or polyamino aromatic compound, which process comprises:
  (a) reacting at ambient pressure and a temperature of between about 0 and 50° C. for between about 0.1 and 24 hr, an electrophilic aromatic compound of the structure:

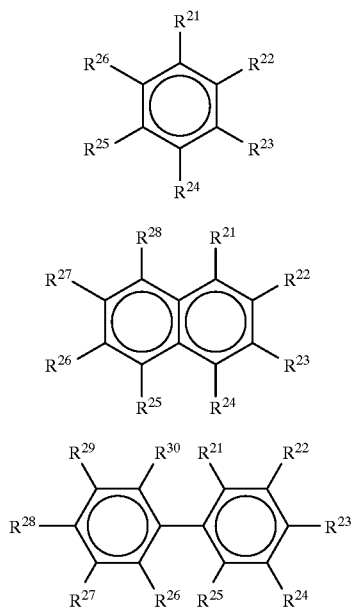

-continued

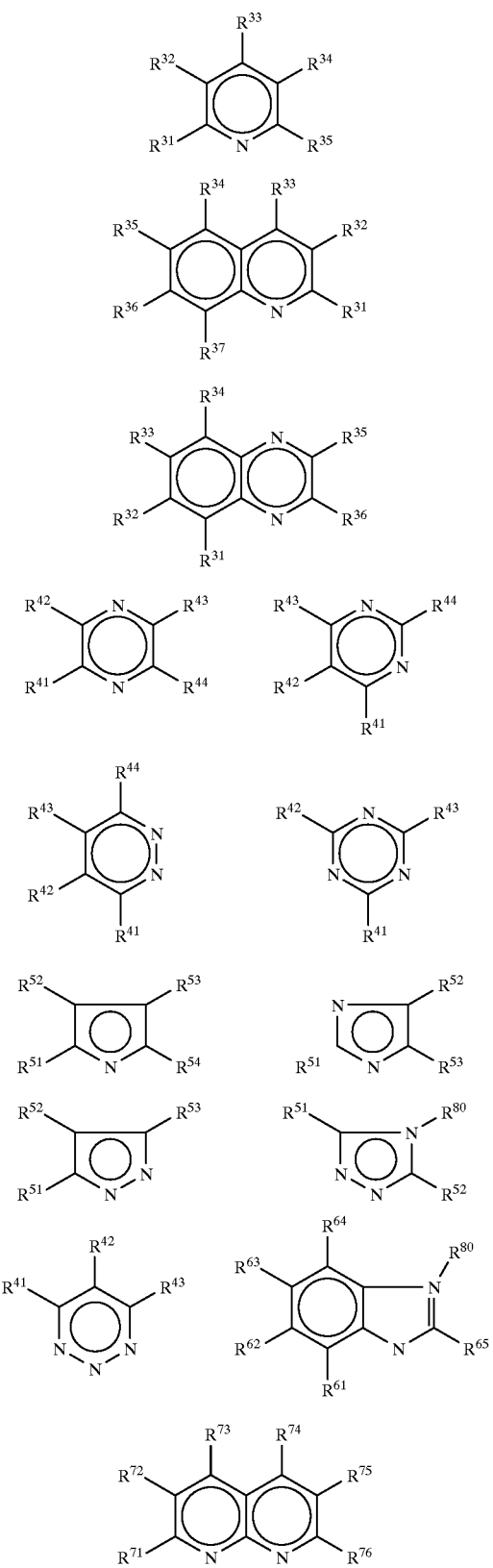

wherein the electron withdrawing group for each structure of groups R$^{21}$ to R$^{37}$, R$^{41}$ to R$^{44}$, R$^{51}$ to R$^{54}$, R$^{61}$ to R$^{65}$, R$^{71}$ to R$^{76}$ and R$^{80}$ is independently selected from the group consisting of —CN, —NO$_2$, —CO$_2$R$_1$, —CONR$_2$, —SO$_2$R, —SO$_3$H, —CF$_3$, —F, —Cl, —Br, —I and —NH$_2$, where R, R$_1$ and R$_2$ are alkyl groups having, from 1 to 6 carbon atoms, with the proviso that at least one of R$^{21}$ to R$^{37}$, R$^{41}$ to R$^{44}$, R$^{51}$ to R$^{54}$, R$^{61}$ to R$^{65}$, R$^{71}$ to R$^{76}$ and R$^{80}$ for each structure is hydrogen, and with the further proviso that for benzene at least one of R$^{21}$ to R$^{26}$ is an electron withdrawing group, and at least one of R$^{21}$ to R$^{26}$ is hydrogen;

for pyridine at least one of R$^{31}$ to R$^{35}$ is an electron withdrawing group, and at least one of R$^{31}$ to R$^{35}$ is hydrogen; and for naphthalene at least one of R$^{21}$ to R$^{28}$ is an electron withdrawing group, and at least one of R$^{21}$ to R$^{28}$ is hydrogen;

for biphenyl, at least one of R$^{21}$ to R$^{30}$ is an electron withdrawing group, and at least one of R$^{21}$ to R$^{30}$ is hydrogen;

for quinoline at least one of R$^{31}$ to R$^{37}$ is an electron withdrawing group, and at least one of R$^{31}$ to R$^{37}$ is hydrogen;

for 1,4-quinoxaline at least one of R$^{31}$ to R$^{36}$ is an electron withdrawing group, and at least one of R$^{31}$ to R$^{36}$ is hydrogen;

for the six-membered rings containing two nitrogen atoms, at least one of R$^{41}$ to R$^{44}$ is an electron withdrawing group, and at least one of R$^{41}$ to R$^{44}$ is hydrogen;

for the six-membered rings containing three nitrogen atoms, at least one of R$^{41}$ to R$^{43}$ is an electron withdrawing group, and at least one of R$^{41}$ to R$^{43}$ is hydrogen; and for the five-membered heterocyclic rings containing one, two, or three nitrogens, at least one of R$^{51}$ to R$^{54}$ is an electron withdrawing group, and at least one of R$^{51}$ to R$^{54}$ is hydrogen, for indole at least one of R$^{61}$ to R$^{65}$ is an electron withdrawing group, and at least one of R$^{61}$ to R$^{65}$ is hydrogen;

for fused pyridine having two six-membered rings, at least one of R$^{71}$ to R$^{76}$ is an electron withdrawing group, and at least one of R$^{71}$ to R$^{76}$ is hydrogen;

wherein R$^{80}$ is alkyl having 1 to 6 carbon atoms;

with an effective amount of reagent selected from the group consisting of:

(i) 1,1,1-tri-G- substituted-hydrazinium salt wherein G is selected from the group consisting of methyl, ethyl, propyl, butyl and benzyl and the anion is selected from the group consisting of chloride, bromide, iodide, fluoride, sulfate, hydroxide, mesylate, triflate, and tetrafluoroborate;

(ii) hydroxylamine;

(iii) O-alkyl hydroxyl amine where alkyl is C$_1$ to C$_{10}$ carbon atoms, or 4-amino-1,2,4-triazole; and combinations thereof;

in the presence of tetraalkyl guanidine wherein alkyl is C$_1$ to C$_{10}$ or alternatively in the presence of a strong base selected from the group consisting of sodium butoxide, potassium butoxide, potassium propoxide, sodium propoxide, sodium ethoxide, potassium ethoxide, sodium methoxide, potassium methoxide, and combinations thereof;

in a solvent selected from the group consisting of methanol, ethanol, propanol, butanol, dimethylsulphoxide, N-methylpyrrolidone, hexamethylphosphoramide, dimethylformamide, dimethylacetamide and mixtures thereof, provided that when alcohols are present primarily DATB and picramide are formed; and (b) isolating the monoamino, diamino or polyamino aromatic compound product of the structure:

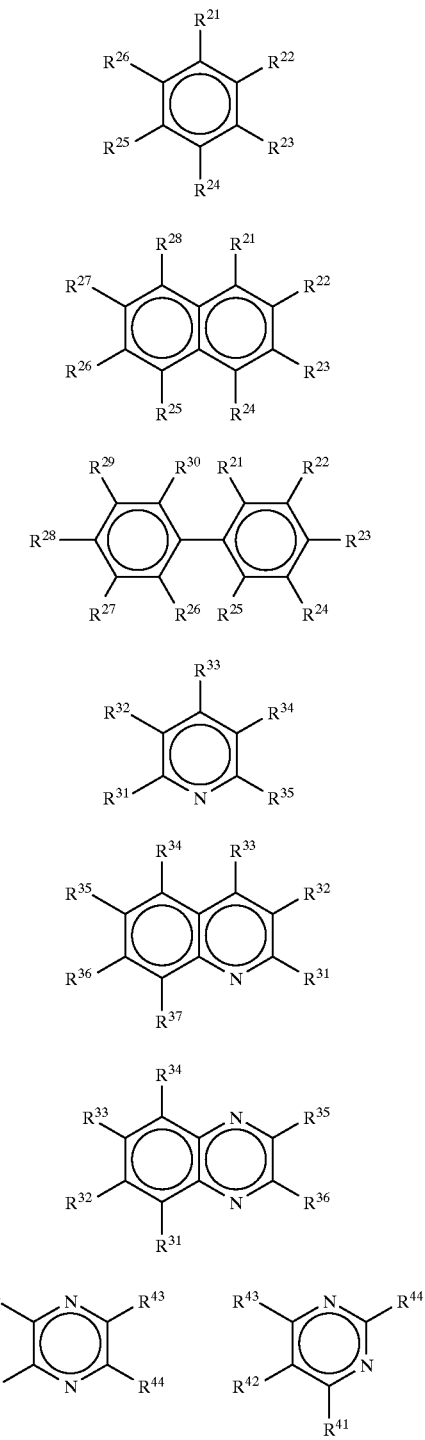

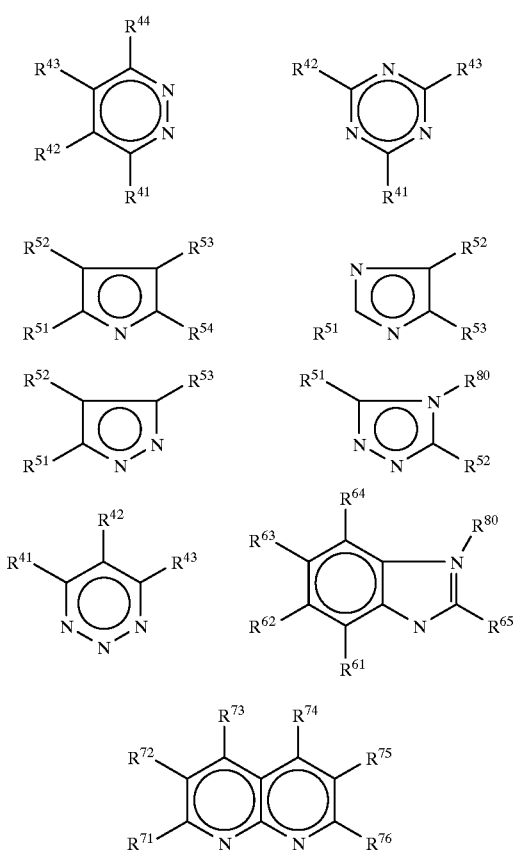

for benzene at least one of $R^{21}$ to $R^{26}$ is an electron withdrawing group, and at least one of $R^{21}$ to $R^{26}$ is an amino group;

for pyridine at least one of $R^{31}$ to $R^{35}$ is an electron withdrawing group, and at least one of $R^{31}$ to $R^{35}$ is an amino group; and for naphthalene, at least one of $R^{21}$ to $R^{28}$ is an electron withdrawing group, and at least one of $R^{21}$ to $R^{28}$ is an amino group;

for biphenyl, at least one of $R^{21}$ to $R^{30}$ is an electron withdrawing group, and at least one on one of $R^{21}$ to $R^{30}$ is an amino group;

for quinoline, at least one of $R^{31}$ to $R^{37}$ is an electron withdrawing group, and at least one of $R^{31}$ to $R^{37}$ is an amino group;

for 1,4- quinoxaline at least one of $R^{31}$ to $R^{36}$ is an electron withdrawing group, and at least one of $R^{31}$ to $R^{36}$ is an amino group;

for the six-membered rings containing two nitrogen atoms at least one of $R^{41}$ to $R^{44}$ is an electron withdrawing group, and at least one of $R^{41}$ to $R^{44}$ is an amino group;

for the six-membered rings containing three nitrogen atoms, at least one of $R^{41}$ to $R^{43}$ is an electron withdrawing group, and at least one $R^{41}$ to $R^{43}$ is an amino group; and for the five-membered heterocyclic rings containing one, two, or three nitrogens, at least one of $R^{51}$ to $R^{54}$ is an electron withdrawing group, and at least one of $R^{51}$ to $R^{54}$ is an amino group, for indole at least one of $R^{61}$ to $R^{65}$ is an electron withdrawing group, and at least one of $R^{61}$ to $R^{65}$ is an amino group;

for fused pyridine have two six-membered rings, at least one of $R^{71}$ to $R^{76}$ is an electron withdrawing group, and at least one of $R^{11}$ to $R^{76}$ is an amino group;

wherein $R^{80}$ is alkyl having 1 to 6 carbon atoms;

wherein the electron withdrawing group is selected from —CN, —$NO_2$, —COR, —$CO_2R_1$, —$CONR_2$, —$SO_2R$, —$SO_3H$, —$CF_3$, —F, —Cl, —Br, —I and —$NH_2$, where $R_1$ and $R_2$ are alkyl having from 1 to 6 carbon atoms.

3. A process to produce 1,3-diamino-2,4,6-trinitrobenzene (DATB) or 1,3,5-triamino-2,4,6,-trinitrobenzene (TATB), which process comprises:

(a) reacting at ambient pressure and a temperature of between about 0 and 50° C. for between about 0.1 and 24 hr, a trinitroaromatic starting material compound V:

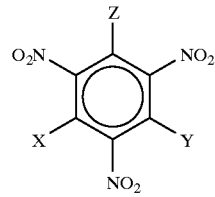

(V)

wherein X, Y, and Z are each independently selected from the group consisting of —H, and —$NH_2$, with the proviso that at least 1 of X, Y, and Z is hydrogen, with an amount effective to produce DATB or TATB of 1,1,1,-trialkylhydrazinium salt wherein alkyl is selected from the group consisting of methyl, ethyl, propyl and butyl and the anion is selected from the group consisting of chloride, bromide, fluoride, iodide, sulfate, hydroxide, mesylate, triflate, tetrafluoroborate and combinations thereof, in the presence of a strong base selected from the group consisting of sodium butoxide, potassium butoxide, potassium propoxide, sodium propoxide, sodium ethoxide, potassium ethoxide, sodium methoxide, potassium methoxide and combinations thereof;

in a solvent selected from the group consisting of methanol, ethanol, propanol, butanol, dimethylsulphoxide, N-methylpyrrolidone, hexamethylphosphoramide, dimethylformamide, dimethylacetamide and mixtures thereof, provided that when alcohols are present primarily DATB and picramide are formed; and (b) isolating the DATB or TATB produced.

4. The process of claim 1 wherein the reaction temperature is between about 10 and 30° C.

5. The process of claim 4 wherein DATB is produced and the 1,1,1-trialkylhydrazinium salt is present in between about 1.9 and 2.3 molar equivalents per mole of starting material compound V.

6. A process of claim 1 to produce 1,3-diamino-2,4,6-trinitrobenzene (DATB) or 1,3,5-triamino-2,4,6,-trinitrobenzene (TATB), which process comprises:

(a) obtaining an aromatic compound as a starting material selected from:

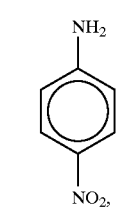 (III)

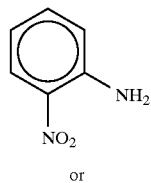 (IV)

or mixtures thereof from commercial sources or by:
(i) reacting

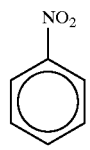

at a temperature of between about 0 and 50° C. for between about 0.1 and 24 hr with an amount effective of 1,1,1-trialkylhydrazinium salt wherein alkyl is selected from the group consisting of methyl, ethyl, propyl and butyl and the salt is selected from the group consisting of chloride, bromide and iodide, in the presence of a base selected from the group consisting of sodium butoxide, potassium butoxide, potassium propoxide, sodium propoxide, sodium ethoxide, potassium ethoxide, sodium methoxide, potassium methoxide and combinations thereof;

in a solvent selected from the group consisting of dimethylsulphoxide, N-methylpyrrolidone, hexamethylphosphoramide, dimethylformamide, dimethylacetamide, and mixtures thereof, and isolating the product consisting of III, IV or combinations thereof;

(ii) or nitrating aniline using a mixture of nitric acid and sulfuric acid to produce consisting of III, IV or combinations thereof; or (iii) nitrating acetanilide using a mixture of nitric acid and sulfuric acid to produce 4-nitroacetanilide and nitrating further using a mixture of nitric acid and sulfuric acid to produce VI;

(b) reacting 2-nitroaniline, 4-nitroaniline or combinations thereof with a nitric acid and sulfuric acid mixture under conditions to produce 2,4,6-trinitroaniline (VI);

(c) reacting at ambient pressure and a temperature of between about 0 and 50° C. for between about 0.1 and 24 hr a trinitro aromatic compound selected from:

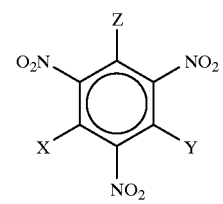 (V)

or

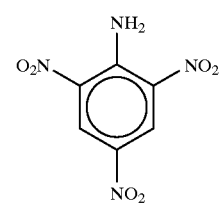 (VI)

wherein X, Y, and Z are each independently selected from the group consisting of —H and —NH$_2$, with the proviso that at least 1 of X, Y, and Z is hydrogen, with an effective amount of 1,1,1-trialkylhydrazinium salt wherein alkyl is selected from methyl, ethyl, propyl and butyl and the anion is selected from the group consisting of chloride, bromide, fluoride, iodide, sulfate, hydroxide, mesylate, triflate, tetrafluoroborate, in the presence of a base selected from the group consisting of sodium butoxide, potassium butoxide, potassium propoxide, sodium propoxide, sodium ethoxide, potassium ethoxide, sodium methoxide, potassium methoxide, and mixtures thereof;

in a solvent selected from the group consisting of methanol, ethanol, propanol, butanol, dimethylsulphoxide, N-methylpyrrolidone, hexamethylphosphoramide, dimethylformamide, dimethylacetamide, and mixtures thereof; and (d) isolating the DATB or TATB produced.

7. A process of claim 1 to produce mono or polyamino-, mono or polynitrobenzene, which process comprises:

(a) obtaining an aromatic compound as a starting material selected from the following structures:

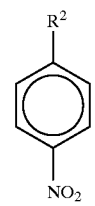

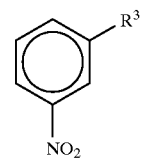

-continued

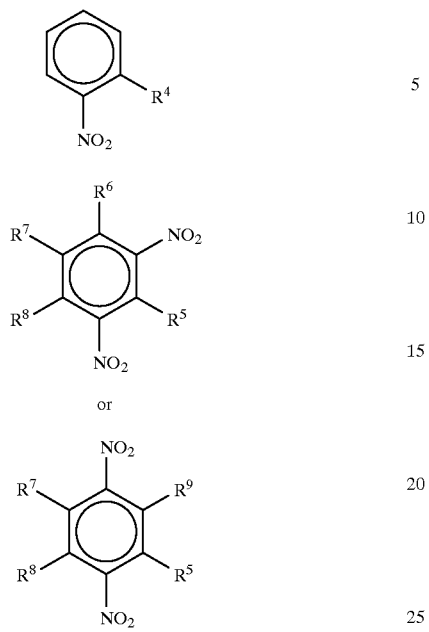

or wherein $R^2$, $R^3$, and $R^4$ are each independently selected from the group consisting of —H, —CH$_3$, F, —Cl, —Br, —I, CN, COOH, COOR and OCH$_3$,
and $R^5$–$R^9$ are each independently selected from the group consisting of —H, —CH$_3$, F, —Cl, —Br, —I, —CN, —OCH$_3$ and mixtures thereof, with the proviso that at least one of $R^5$–$R^9$ is H;

(b) reacting at ambient pressure and a temperature of between about 0 and 50° C. for between about 0.1 and 24 hr a nitroaromatic compound;
with an effective amount of 1,1-di J-substituted-1,2-di-r-hydrazinium salt wherein dialkyl is selected from methyl, ethyl, propyl, butyl, hexyl, cyclohexyl, dodecyl, pyridyl, —CH$_2$ (CH$_2$)$_n$ CH$_2$—, and —(CH$_2$CH$_2$)O(CH$_2$CH$_2$)—, where n is between 1 to 10, R is selected from the group consisting of H, C$_1$–C$_{20}$ alkyl and aryl, and the anion is selected from the group consisting of chloride, bromide, fluoride, iodide, sulfate, hydroxide, mesylate, triflate, and tetrafluoroborate,
in the presence of a base selected from the group consisting of sodium butoxide, potassium butoxide, potassium propoxide, sodium propoxide, sodium ethoxide, potassium ethoxide, sodium methoxide, potassium methoxide and mixtures thereof;
in a solvent selected from the group consisting of methanol, ethanol, propanol, butanol, dimethylsulphoxide, N-methylpyrrolidone, hexamethylphosphoramide, dimethylformnamide, dimethylacetamide and mixtures thereof; and (C) isolating the monoamino, diamino or triaminosubstituted nitroaromatic compound produced.

8. The process of claim 1 to produce 1,3-diamino-2,4,6-trinitrobenzene (DATB) or 1,3,5-triamino-2,4,6,-trinitrobenzene (TATB), which process comprises:

(a) reacting at ambient pressure and a temperature of between about 0 and 50° C. for between about 0.1 and 24 hr, a trinitroaromatic starting material compound of the structure:

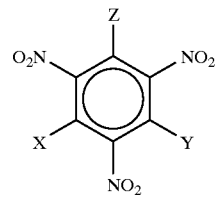

wherein X, Y, and Z are each independently selected from the group consisting of —H and —NH$_2$, with the proviso that at least 1 of X, Y, and Z is hydrogen;
with an effective amount of 4-amino-1,2,4-triazole, hydroxylamine or O-alkyl hydroxylamine wherein alkyl has 1 to 10 carbon atoms, provided that hydroxylamine and O-alkyl hydroxylamine, when used, produce primarily DATB;
in the presence of a strong base selected from the group consisting of sodium butoxide, potassium butoxide, potassium propoxide, sodium propoxide, sodium ethoxide, potassium ethoxide, sodium methoxide, potassium methoxide and combinations thereof;
in a solvent selected from the group consisting of methanol, ethanol, n-propanol, iso-propanol, n-butanol, iso-butanol, sec-butanol, tert-butanol, dimethylsulphoxide, N-methylpyrrolidone, hexamethylphosphoramide, dimethylformamide, dimethylacetamide and mixtures thereof, provided that when alcohols are present primarily DATB is formed; and (b) isolating the DATB or TATB produced.

9. The process of claim 1 wherein
the trinitroaromatic starting material compound is selected from 1,3,5-trinitrobenzene, 2,4,6-trinitroaniline, or 1,3-diamino-2,4,6-trinitrobenzene;
the strong base is selected from sodium methoxide and the solvent is selected from dimethylsulphoxide, N-methylpyrrolidone, hexamethylphosphoramide, dimethylformamide, dimethylacetamide or mixtures thereof.

10. The process of claim 1 to produce 1,3-diamino-2,4, 6-trinitrobenzene (DATB) or 1,3,5-triamino-2,4,6,-trinitrobenzene (TATB), which process comprises:

(a) obtaining an aromatic starting material compound of the structure:

(III)

(IV)

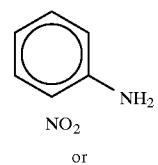

or mixtures thereof from commercial sources or by:
(i) reacting

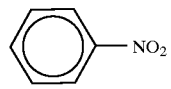

with an amount of 4-amino-1,2,4-triazole, hydroxylamine, effective to produce compound III or IV, or mixtures thereof;
in the presence of a base selected from the group consisting of sodium butoxide, potassium butoxide, potassium propoxide, sodium propoxide, sodium ethoxide, potassium ethoxide, sodium methoxide, potassium methoxide, and combinations thereof;
in a solvent selected from the group consisting of dimethylsulphoxide, N-methylpyrrolidone, hexamethylphosphoramide, dimethylformamide, dimethylacetamide and mixtures thereof, or isolating the product which is III;
(ii) or nitrating aniline using a mixture of nitric acid and sulfuric acid to produce compound III, compound IV or combinations thereof; or
(iii) nitrating acetanilide using a mixture of nitric acid and sulfuric acid to produce 4-nitroacetanilide and nitrating further using a mixture of nitric acid and sulfuric acid to produce compound VI;
(b) reacting 2-nitroaniline, 4-nitroaniline or combinations thereof with a nitric acid, and sulfuric acid mixture under conditions to produce 2,4,6-trinitroaniline;
(A) reacting at temperature of between about 0 and 50° C. for between about 0.1 and 24 hr a trinitroaromatic starting material compound:

(V)

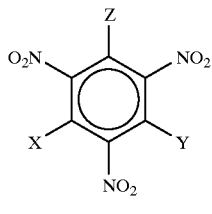

or (VI)

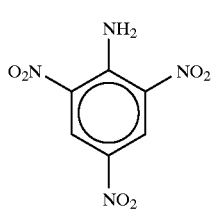

wherein X, Y, and Z are each independently selected from the group consisting of —H and —NH$_2$, with the proviso that at least one of X, Y, and Z is hydrogen;
with an effective amount of 4-amino-1,2,4-triazole, hydroxylamine, or O-alkylhydroxylamine where alkyl has 1 to 10 carbon atoms;
in the presence of a base selected from the group consisting of sodium butoxide, potassium butoxide, potassium propoxide, sodium propoxide, sodium ethoxide, potassium ethoxide, sodium methoxide, potassium methoxide and mixtures thereof;
in a solvent selected from the group consisting of methanol, ethanol, propanol, butanol, dimethylsulphoxide, N-methylpyrrolidone, hexamethylphosphoramide, dimethylformamide, dimethylacetamide and mixtures thereof provided that when an alcohol is present or when hydroxylamine or its O-alkyl hydroxylamine replaces 4-amino-1,2,4-triazole, primarily DATB is produced; and
(B) isolating the DATB or TATB produced.

11. A process to produce 1,3,5-triamino-2,4,6,-trinitrobenzene (TATB), which process comprises:
(a) reacting at ambient pressure and a temperature of between about 70 and 100° C. for between about 0.1 and 24 hr, a trinitroaromatic starting material compound of the structure:

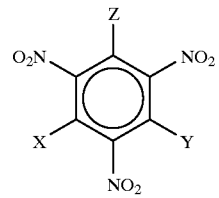

wherein X, Y, and Z are each independently selected from the group consisting of —H and —NH$_2$, with the proviso that at least 1 of X, Y, and Z is hydrogen;
with an effective amount of a VNS reagent selected from the group consisting of alkyl hydrazinium halide wherein alkyl has 1 to 6 carbon atoms, 4-amino-1,2,4-triazole, hydroxylamine or O-alkyl hydroxylamine wherein alkyl has 1 to 10 carbon atoms;
in the presence of a strong base selected from the group consisting of sodium butoxide, potassium butoxide, potassium propoxide, sodium propoxide, sodium ethoxide, potassium ethoxide, sodium methoxide, potassium methoxide and combinations thereof;
in a solvent selected from the group consisting of methanol, ethanol, n-propanol, iso-propanol, n-butanol, iso-butanol, sec-butanol, tert-butanol, dimethylsulphoxide, N-methylpyrrolidone, hexamethylphosphoramide, dimethylformamide, dimethylacetamide and mixtures thereof, provided that when alcohols are present primarily DATB is formed; and
(b) isolating the TATB produced.

12. The process of claim 11 wherein the reaction temperature is between about 80 and 100° C.; and hydroxylamine is used.

13. The process of claim 11 wherein TATB is produced and the hydroxylamine is present in step (a) in between about 3.9 and 5.5 molar equivalents per mole of the trinitroaromatic starting material compound.

14. The process of claim 11 wherein the trinitroaromatic starting material compound is selected from the group consisting of 1,3,5-trinitrobenzene, 2,4,6-trinitroaniline and 1,3-diamino-2,4,6-trinitrobenzene.

15. The process of claim 11 wherein the 4-amino-1,2,4-triazole is present in between about 3.9 and 5.5 mole eq.

16. The process of claim 11 wherein the strong base is selected from the group consisting of sodium ethoxide and potassium tert-butoxide.

17. The process of claim 11 wherein
the starting material compound is selected from 1,3,5-trinitrobenzene and, 2,4,6-trinitroaniline;
the strong base is selected from the group consisting of sodium ethoxide and potassium tert-butoxide; and
the solvent is DMSO, and hydroxylamine is used.

18. A process for the production of quaternary alkyl hydrazine in situ for subsequent reaction as an aminating agent, which process comprises:
(a) reacting an alkyl substituted unsymmetrical hydrazine with an alkylating agent selected from the group consisting of alkyl halide and dimethyl sulfate at between about 10 and 50° C. for between about 0.1 and 4 hours in a solvent to produce the quaternary alkyl hydrazine.

19. The process of claim 18 wherein
in the alkyl halide, alkyl is selected from the group consisting of alkyl having 1 to 6 carbon atoms and halide is selected from the group consisting of Cl, Br and I,
in the dialkyl sulfate the alkyl is from C1 to C6,
the temperature is between about 20 and 50° C.,
the time is between about 0.5 and 2.0 hours; and
the dipolaraprotic solvent is selected from the group consisting of dimethylsulphoxide, N-methylpyrrolidone, hexamethylphosphoramide, dimethylformamide, dimethylacetamide and mixtures thereof.

20. The process of claim 3 wherein said process is conducted using a quaternary hydrazine generated in situ in step (a) at between about 70 and 100° C. for between about 0.5 and 24 hours; and
said process in step (a) further includes tetralkyl guanidine wherein alkyl is selected from the group consisting of alkyl having 1 to 6 carbon atoms.

* * * * *